United States Patent
Tajima

(10) Patent No.: US 9,778,253 B2
(45) Date of Patent: Oct. 3, 2017

(54) TUBE FOR MEASURING BIO-RELATED SUBSTANCE AND QUANTIFYING SYSTEM

(75) Inventor: Hideji Tajima, Chiba (JP)

(73) Assignee: UNIVERSAL BIO RESEARCH CO., LTD., Matsudo-shi (JP)

(*) Notice: Subject to any disclaimer, the term of this patent is extended or adjusted under 35 U.S.C. 154(b) by 468 days.

(21) Appl. No.: 13/265,078

(22) PCT Filed: Apr. 20, 2010

(86) PCT No.: PCT/JP2010/056971
§ 371 (c)(1),
(2), (4) Date: Dec. 7, 2011

(87) PCT Pub. No.: WO2010/122990
PCT Pub. Date: Oct. 28, 2010

(65) Prior Publication Data
US 2012/0094307 A1 Apr. 19, 2012

(30) Foreign Application Priority Data
Apr. 20, 2009 (JP) .................................. 2009-102379

(51) Int. Cl.
*G01N 33/543* (2006.01)
*G01N 21/64* (2006.01)
(Continued)

(52) U.S. Cl.
CPC ... *G01N 33/54313* (2013.01); *G01N 21/6428* (2013.01); *G01N 21/274* (2013.01); *G01N 2021/0325* (2013.01)

(58) Field of Classification Search
CPC ............. G01N 21/274; G01N 21/6428; G01N 33/54313; G01N 33/54333
(Continued)

(56) References Cited

U.S. PATENT DOCUMENTS 5,776,694 A * 7/1998 Sheiness et al. ............. 435/6.15
5,879,881 A * 3/1999 Rubenstein .......... C12Q 1/6834
422/422
(Continued)

FOREIGN PATENT DOCUMENTS

CA 2 748 364 A1 7/2010
EP 1 541 993 A2 6/2005
(Continued)

OTHER PUBLICATIONS

Extended European Search Report dated Oct. 17, 2012, in European Patent Application No. 10767047.3.
(Continued)

*Primary Examiner* — Chris L Chin
(74) *Attorney, Agent, or Firm* — Birch, Stewart, Kolasch & Birch, LLP

(57) ABSTRACT

A bio-related substance assay tube 2 comprises a target substance capture bead 3 serving as a first microparticle, compensation bead 4 serving as a second microparticle on which a given amount of a bio-related substance has been immobilized, and a negative control bead 5 serving as a third microparticle for use as a negative control. A mount unit 12 comprises a nozzle communicating with a pump, and the bio-related substance assay tube 2 is mounted in the mount unit 12 to ensure communication with this nozzle. An analyte is introduced into the bio-related substance assay tube 2, followed by labeling the bio-related substance bound to each microparticle to cause light emission. Based on light emission from each microparticle, a calibration curve is prepared or the emission intensity of the first microparticle is compensated to quantify the bio-related substance.

10 Claims, 20 Drawing Sheets

(51) Int. Cl.
  *G01N 21/27* (2006.01)
  *G01N 21/03* (2006.01)

(58) Field of Classification Search
  USPC .................................. 436/501; 422/549, 69
  See application file for complete search history.

(56) References Cited

U.S. PATENT DOCUMENTS

| | | | |
|---|---|---|---|
| 6,632,655 B1 | 10/2003 | Mehta et al. | |
| 6,696,304 B1* | 2/2004 | Davies | 436/518 |
| 2001/0009763 A1 | 7/2001 | Kambara et al. | |
| 2004/0239924 A1* | 12/2004 | Couderc | G01N 21/645 356/318 |
| 2004/0241700 A1 | 12/2004 | Lamont et al. | |
| 2007/0184456 A1 | 8/2007 | Chee et al. | |
| 2009/0137411 A1 | 5/2009 | Sun et al. | |
| 2009/0221080 A1 | 9/2009 | Tajima | |
| 2009/0298094 A1* | 12/2009 | Kohara et al. | 435/7.9 |

FOREIGN PATENT DOCUMENTS

| | | |
|---|---|---|
| EP | 1821106 A1 * | 8/2007 |
| EP | 1 930 724 A1 | 6/2008 |
| JP | 2001-83153 A | 3/2001 |
| JP | 2005-504988 A | 2/2005 |
| JP | 2005-114532 A | 4/2005 |
| JP | 2007-530925 A | 11/2007 |
| WO | WO 2006/109866 A1 | 10/2006 |
| WO | WO 2007/029616 A1 | 3/2007 |
| WO | WO 2010/074265 A1 | 7/2010 |

OTHER PUBLICATIONS

Yingyongnarongkui et al., "Parallel and Muliplexed Bead-Based Assays and Encoding Strategies," Combinatorial Chemistry & High Throughput Screening (2003), vol. 6, pp. 577-587.

* cited by examiner

TUBE FOR MEASURING BIO-RELATED SUBSTANCE AND QUANTIFYING SYSTEM

TECHNICAL FIELD

The present invention relates to an assay tube for a bio-related substance, and a quantification system using this tube.

BACKGROUND ART

In the field of medical practice, tests are often conducted to determine the concentration of a specific component in an analyte (e.g., a serum sample) taken from a subject. In recent years, devices for automatically calculating the concentration of a specific component in a serum sample have been used widely in these tests, thus leading to a reduction in the time and labor required for testing. However, even in the case of using such a device, to ensure reliable quantification of a target substance in an analyte, reagents to be used should be confirmed for their performance, lots, features and so on in various tests.

In conventional techniques for quantification of a target substance in an analyte, negative and positive control experiments, measured value compensation and the like are conducted separately, followed by comparison with the measured value obtained from the target substance to thereby determine an accurate value. For this reason, there were some cases where rapid quantification was difficult to perform on a target substance or where the resulting accuracy was low. Moreover, to maintain the accuracy of measurement, a calibration curve was prepared in some cases before measurement of components in an analyte, which made it difficult to increase working efficiency because considerable time was required for quantification of a target component. Furthermore, when attempting to quantify multiple target bio-related substances, considerable time and effort were often required.

DISCLOSURE OF THE INVENTION

Problem to be Solved by the Invention

The present invention has been made in consideration of the above situation and aims t o achieve more accurate quantification of a bio-related substance with simpler handling. Moreover, the present invention also aims to provide a quantification system which allows more accurate quantification of a target bio-related substance.

Means to Solve the Problem

As a result of extensive and intensive efforts made to solve the above problems, the inventors of the present invention have found that a target bio-related substance can be quantified more accurately when a single bio-related substance assay tube is designed to comprise an assay particle used to measure the target bio-related substance and a compensation particle intended to increase the accuracy of a measured value.

Namely, the present invention is directed to a bio-related substance assay tube, which comprises a first microparticle on which a substance capable of binding to a target bio-related substance to be measured is immobilized, a second microparticle on which the above bio-related substance is immobilized in a given amount, and a third microparticle for use as a negative control, wherein these microparticles are aligned in the tube. In the context of the present invention, the microparticle for use as a negative control is intended to mean a particle not binding to a target bio-related substance. Such a microparticle for use as a negative control may be, for example, an analyte blank prepared by removing a target bio-related substance from an analyte.

In the bio-related substance assay tube of the present invention, the above second microparticle is a microparticle for compensation of data measured for a bio-related substance, and preferably comprises a plurality of microparticles on which gradually different amounts of a bio-related substance are immobilized. This microparticle is used for preparation of a calibration curve. Moreover, in the present invention, light-shielding members may further be interposed to separate the above first to third microparticles.

It is desirable to use a calibration curve for quantification of a bio-related substance, and this calibration curve is desirably prepared during quantification of the bio-related substance or before quantification of the bio-related substance.

For quantification of a target bio-related substance, a microparticle on which a substance capable of binding to the target bio-related substance is immobilized is used together with a microparticle for use as a positive control and a microparticle for use as a negative control to thereby confirm the accuracy of quantification.

The quantification system of the present invention comprises the above tube, a detection unit for detecting signals emitted from the microparticles in the above tube, a calibration curve preparation unit for preparing a calibration curve based on the signals detected above, and an arithmetic unit for quantifying a bio-related substance by referring to the calibration curve prepared above.

Alternatively, the quantification system of the present invention comprises:

a fluorescence intensity calculation means, in which fluorescent labels are provided to a first microparticle capable of binding to a target bio-related substance, a second microparticle on which a given amount of the target bio-related substance has been immobilized and which serves as a positive control, and a third microparticle which serves as a negative control, and these fluorescently labeled first to third microparticles are irradiated with excitation light to calculate their fluorescence intensity; and an arithmetic means, which receives fluorescence intensity signals sent from the fluorescence intensity calculation means to quantify the above bio-related substance bound to the first microparticle.

On the second microparticle, gradually different amounts of the bio-related substance may be immobilized before use in order to prepare a calibration curve for quantification of the target bio-related substance bound to the first microparticle, or alternatively, a known amount of the bio-related substance may be immobilized in order to compensate the emission intensity of the first microparticle. The first to third microparticles may be aligned and fixed in the tube before use or may be aligned during measurement of the bio-related substance. The tube in which the first to third microparticles are aligned may preferably be configured removably.

Furthermore, the present invention is directed to a method for measuring a bio-related substance, which comprises contacting an analyte with the above tube, and measuring the target bio-related substance in the analyte. In the present invention, qualitative detection and quantification can be simultaneously performed on a target bio-related substance during measurement.

Effect of the Invention

The bio-related substance assay tube of the present invention allows compensation for measurement of a bio-related substance and hence more accurate quantification of the bio-related substance.

Moreover, by using a second bead for use as a positive control, a third bead for use as a negative control, and a fourth bead for compensation purposes, a target bio-related substance can be quantified more accurately while saving the effort required for correction of the system even when there are differences in the lot number or serial number of assay tubes, the model name or model number of quantification systems, and the type of reagents used for quantification, etc.

In this way, the tube and system of the present invention allow not only qualitative detection of the presence or absence of a target bio-related substance, but also quantification of the amount of the target bio-related substance, and hence enable the provision of a more convenient quantification system. This means that the present invention is useful as an alternative system to replace immunochromatography because the present invention allows quantification of the amount of a reaction product simultaneously with confirmation of qualitative reaction which has been performed by immunochromatography, etc.

Thus, the assay tube and quantification system of the present invention enable the provision of a more convenient quantification system. Moreover, the assay tube of the present invention or a quantification system using this assay tube can save the effort required for service and maintenance of the system and can be fully adapted to perform point-of-care testing for rapid diagnosis in the vicinity of a patient.

BEST MODES FOR CARRYING OUT THE INVENTION

1. Summary of the Invention

The bio-related substance assay tube of the present invention comprises a first microparticle on which a substance capable of binding to a target bio-related substance to be measured is immobilized, a second microparticle on which the above bio-related substance is immobilized in a given amount, and a third microparticle for use as a negative control, wherein these microparticles are aligned in the tube. By using the bio-related substance assay tube of the present invention, two types of different quantification procedures can be performed on a bio-related substance. Namely, the first quantification procedure (i) is intended to compensate the value measured for a target bio-related substance using a previously prepared calibration curve to thereby achieve more accurate quantification, while the second quantification procedure (ii) is intended to simultaneously perform preparation of a calibration curve and quantification of a target bio-related substance to thereby achieve more accurate quantification. In the first quantification procedure (i), a signal curve obtained for predetermined amounts of a target bio-related substance to be measured is used as a calibration curve, and the first procedure is intended for cases where a bio-related substance is immobilized on a microparticle in an amount corresponding to any position on this calibration curve. This microparticle is used for measured value compensation. On the other hand, the second quantification procedure (ii) is intended for cases where different amounts of a bio-related substance are immobilized on a plurality of microparticles. These microparticles on which different amounts of a bio-related substance are immobilized are used for preparation of a calibration curve.

Figure 1:
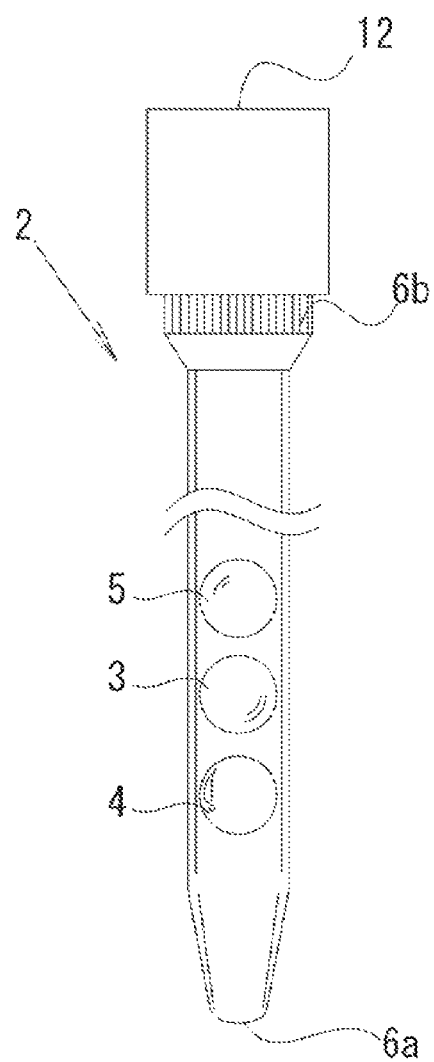
FIG. 1 schematically shows the bio-related substance assay tube of the present invention, in which a target substance capture bead, a negative control bead, and a compensation bead are aligned.

As described above, in the first quantification procedure (i), the second microparticle is used to compensate the value measured for the bio-related substance captured by the first microparticle. The first embodiment for the bio-related substance assay tube of the present invention is intended to use the second microparticle for the purpose of compensating the value measured for the bio-related substance captured by the first microparticle, and the bio-related substance assay tube shown in FIG. 1 can be presented as an example for this purpose. The bio-related substance assay tube 2 shown in FIG. 1 comprises a target substance capture bead 3 serving as a first microparticle, a compensation bead 4 serving as a second microparticle on which a given amount of a bio-related substance has been immobilized, and a negative control bead 5 serving as a third microparticle for use as a negative control.

Figure 2:
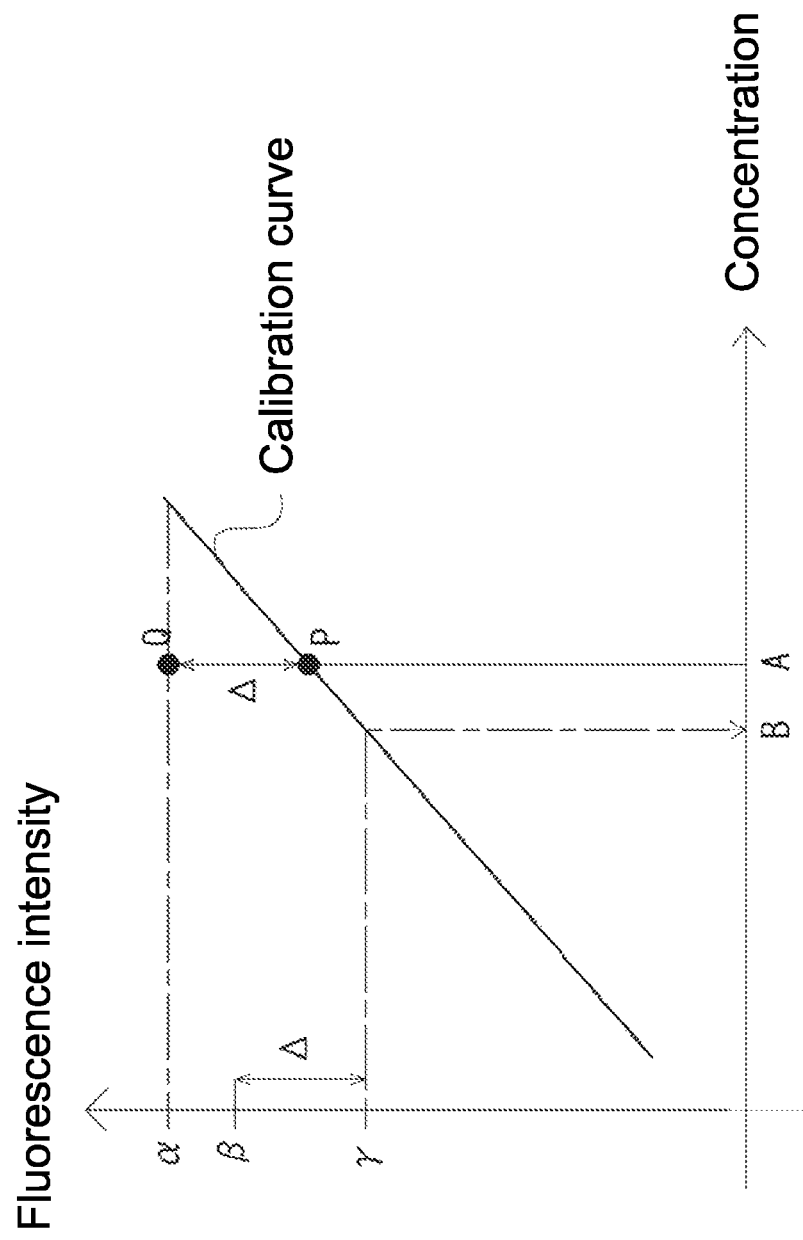
FIG. 2 briefly illustrates procedures for measured value compensation using the emission intensity and concentration of a compensation bead.

In a case where the second microparticle is used to compensate the value measured for the bio-related substance captured by the first microparticle, for example when an analyte is introduced into the tube and contacted with the microparticles, followed by measurement of signals (e.g., emission intensity) from the bio-related substance immobilized on the second microparticle, the measured emission intensity may be displaced from the value (on a calibration curve) predicted from the amount of the bio-related substance immobilized on the second microparticle. In such a case, a displacement Δ (delta) from the calibration curve is calculated and this displacement Δ is incorporated into the data measured for the target substance capture bead to obtain the quantified value of the bio-related substance. By quantifying a bio-related substance according to such a procedure, errors in the quantification of the target bio-related substance can be reduced to thereby achieve more accurate quantification. For example, as shown in FIG. 2, a bio-related substance is immobilized on the second microparticle in a predetermined amount (in an amount corresponding to any position on a calibration curve), and the emission intensity for the second microparticle is expected to be plotted, for example, at position P on the calibration curve against the concentration A. However, if the actual measured value of emission intensity is plotted at position Q above the calibration curve, there is a displacement Δ of emission intensity between the plots P and Q. This displacement Δ can be used as a compensation parameter for emission intensity. For compensation of emission intensity, this displacement Δ may be, for example, subtracted from the actual measured value of emission intensity for the first microparticle on which a substance capable of binding to the target bio-related substance to be measured is immobilized. If the emission intensity of the first microparticle is β, the concentration B corresponding to the value γ, which is calculated by subtracting the displacement Δ from β, can be obtained as a more accurate quantified value. When the concentration corresponding to this subtracted emission intensity is determined from the calibration curve, quantification of the bio-related substance bound to the first microparticle can be accomplished with higher accuracy. On the other hand, if the emission intensity of the second microparticle corresponding to the concentration A is plotted below the calibration curve, the displacement Δ may be added to the actual measured value of emission intensity for the first microparticle to compensate the emission intensity. When the concentration corresponding to this added emission intensity is determined from the calibration curve, quantification of the bio-related substance bound to the first microparticle can be accomplished with higher accuracy. It should be noted that such an approach to compensation of emission intensity can be applied not only to the above emission intensity, but also to other measurements (e.g., absorbance), and may be modified as appropriate to suit the configuration of a quantification system.

Figure 3:
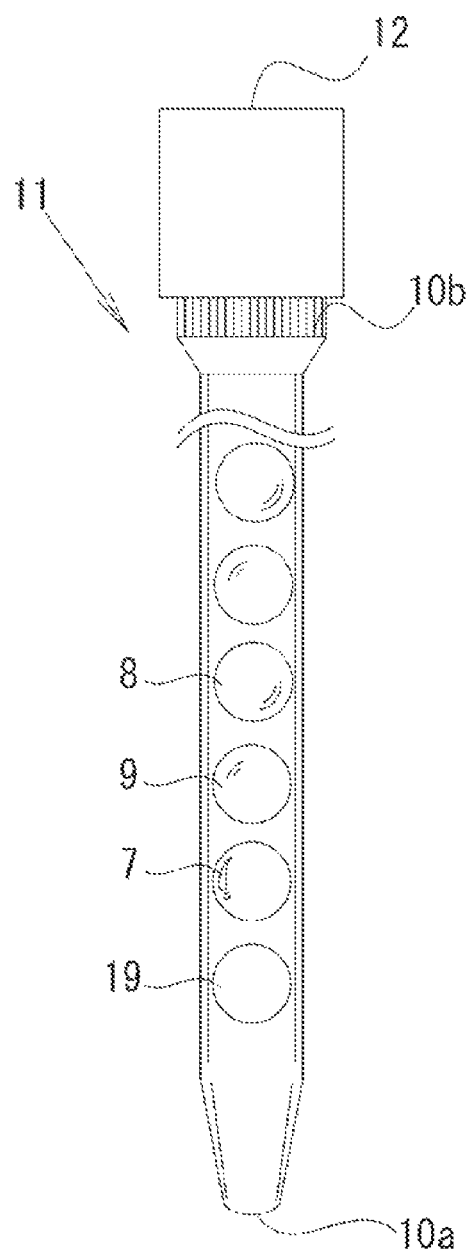
FIG. 3 schematically shows the bio-related substance assay tube of the present invention, in which a first microparticle and a plurality of second microparticles are aligned.

In the second quantification procedure (ii), preparation of a calibration curve and quantification of a target bio-related substance based on this calibration curve can be performed almost at the same time. An embodiment of a bio-related substance assay tube which simultaneously allows preparation of a calibration curve and quantification of a target bio-related substance is as shown in FIG. 3, by way of example. As shown in FIG. 3, a bio-related substance assay tube 11 comprises a first microparticle 7 on which a substance capable of binding to a target bio-related substance to be measured is immobilized, a plurality of microparticles (second microparticles) 8 and 9 on which different amounts of the above bio-related substance have been immobilized, and a negative control bead 19 serving as a third microparticle for use as a negative control. The number of microparticles on which different amounts of the bio-related substance have been immobilized may be, for example, two as shown in the figure, and the amount of the bio-related substance immobilized on each of these two microparticles 8 and 9 may be measured and plotted on a graph to thereby prepare a calibration curve. It should be noted that although two microparticles on which different amounts of the bio-related substance have been immobilized are shown as an example, the number of such microparticles is not limited to two and may be two or more (e.g., three or four microparticles). With increasing the number of microparticles on which different amounts of a bio-related substance have been immobilized, deviations in the preparation of a calibration curve can be reduced to prepare a more reliable calibration curve.

Figure 4:
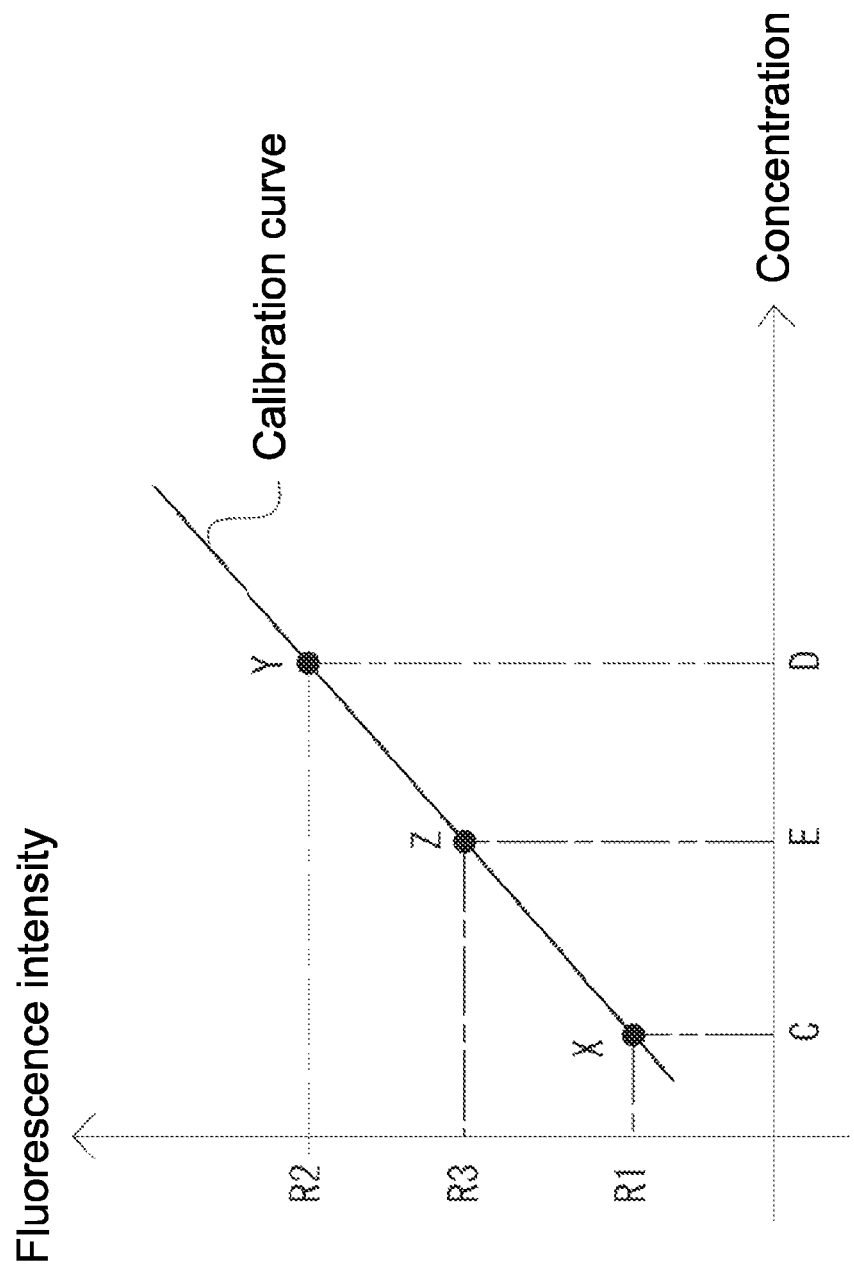
FIG. 4 briefly illustrates how to quantify the target substance concentration from a calibration curve prepared based on the emission intensity and known concentration of each of beads carrying different amounts of antibody immobilized thereon.

By comprising a first microparticle 7 on which a substance capable of binding to a target bio-related substance is immobilized and a plurality of microparticles 8 and 9 on which different amounts of the above bio-related substance have been immobilized, preparation of a calibration curve and quantification of a target bio-related substance can be performed at the same time to achieve measurement with fewer measurement errors. In such an embodiment, for example, as shown in FIG. 4, the point X on the graph is plotted from the emission intensity R1 and known concentration of the microparticle 8, while the point Y on the graph is plotted from the emission intensity and known concentration of the microparticle 9. These points X and Y may be used to prepare a calibration curve, and the prepared calibration curve can be used to quantify the concentration of a target substance to be measured. Namely, the microparticles and an analyte may be contacted to determine the concentration E from the calibration curve on the basis of the emission intensity R3 of the microparticle 7. In view of the foregoing, more accurate quantification can be achieved by simultaneously performing preparation of a calibration curve and quantification of a target bio-related substance.

Such quantification as shown above allows compensation for measurement of a bio-related substance and hence more accurate quantification of the bio-related substance.

Moreover, by using a first microparticle which captures a bio-related substance, a second microparticle on which a given amount of the bio-related substance has been immobilized, and a third microparticle for use as a negative control, the target bio-related substance can be quantified more accurately while saving the effort required for correction of the system even when there are differences in the lot number or serial number of assay tubes, the model name or model number of quantification systems, and the type of reagents used for quantification, etc. In this way, the assay tube and quantification system of the present invention enable the provision of a more convenient quantification system.

Further, the assay tube of the present invention or a quantification system using this assay tube can save the effort required for service and maintenance of the system and can be fully adapted to perform point-of-care testing for rapid diagnosis in the vicinity of a patient.

In these embodiments, each microparticle is formed into an approximately spherical shape and preferably has a particle size of 0.05 to 10.0 mm, more preferably 0.1 to 5.0 mm. Materials for the microparticles include, for example, silicon nitride, silica, glass, magnetite, polystyrene, polyvinyl chloride, polyethylene, polypropylene, polycarbonate, nylon, polyacrylamide, dextran, amylose, agarose, natural and modified celluloses, activated carbon, etc.

Techniques used for measurement include, for example, those based on chemiluminescence, those based on bioluminescence, those based on fluorescence, etc.

In a case where chemiluminescence is used to quantify a bio-related substance, a chemiluminescent substance excited by chemical reaction will emit electromagnetic waves into the external environment when transferred to the ground state. For protein quantification, an emission system causing such an event is typically exemplified by luminol- and dioxetane-based systems.

In luminol-based chemiluminescence, luminol will produce light emission when decomposed in the presence of hydrogen peroxide, and will be able to produce stronger light emission if peroxidase is used as a catalyst. Moreover, upon addition of an iodophenol compound, its emission intensity can be enhanced approximately 1000-fold; the use of such an enhancer achieves not only enhanced emission intensity, but also extended emission time. Commercially available products which cause light emission in this way include, for example, SuperSignal® series (Pierce Chemical), ImmunoStar Kit (Wako Pure Chemical Industries, Ltd., Japan), BM Chemiluminescence (Roche Diagnostics), etc.

In dioxetane-based chemiluminescence, a chemiluminescent substance (e.g., AMPPD®) will react with alkaline phosphatase to generate an intermediate, and this intermediate will be spontaneously cleaved to generate adamantanone and a luminescent substance in an excited state. This luminescent substance will produce light emission until it reaches the ground state. Commercially available products which achieve light emission in this way include, for example, Immun-Star kit (Bio-Rad Laboratories, Inc.), Phototope® (New England Bio Labs), etc.

On the other hand, in a case where fluorescence is used to quantify a target bio-related substance, the target bio-related substance is provided with a fluorescent label, and this fluorescent label is irradiated with excitation light at a specific wavelength to cause fluorescence emission from the fluorescent label. For this reason, the configuration required in this case differs from that of the above chemiluminescence-based measurement system. In the case of using fluorescence, it is generally possible to simultaneously detect multiple bio-related substances of different types, e.g., because multiple staining can be performed on bio-related substances and/or fluorescence emission can be caused at any desired time. This fluorescence-based measurement system will be described later in more detail.

In this way, the present invention enables not only qualitative detection but also quantification of a target bio-related substance at the same time.

2. Bio-Related Substance

In the context of the present invention, the term "bio-related substance" refers to a substance to be quantified or detected, which is contained in a sample, and is intended to mean any biosubstance including microorganisms (bacteria), viruses, parasites, cells, nucleic acids, polysaccharides, proteins (peptides, hormones, receptors, enzymes), antigens, antibodies, toxins, pathogens, small molecules or the like.

Microorganisms include fungi as well as eubacteria and archaebacteria. Examples of fungi include those of the genera *Saccharomyces, Aspergillus, Candida*, etc. Examples of eubacteria include microorganisms belonging to the genera *Mycobacterium, Escherichia, Bacillus, Listeria, Vibrio, Salmonella, Pseudomonas, Staphylococcus, Mycoplasma, Rickettsia, Chlamydia*, etc. Examples of archaebacteria include those of the genera *Thermoplasma, Halobacterium, Methanobacterium*, etc. More specific examples include the species *Saccharomyces cerevisiae, Aspergillus nidulans, Candida albicans, Mycobacterium tuberculosis, Mycobacterium avium, Mycobacterium intracellulare, Mycobacterium kansasii, Escherichia coli, Bacillus cereus, Bacillus anthracis, Listeria monocytogenes, Vibrio parahaemolyticus, Vibrio cholerae, Salmonella typhi, Pseudomonas aeruginosa, Staphylococcus aureus, Mycoplasma pneumoniae, Rickettsia prowazekii, Chlamydia trachomatis*, etc.

Viruses include, for example, those of the families Adenoviridae, bacteriophage, Retroviridae, etc. More specific examples include adenovirus, T7-like virus, hepatitis B virus, hepatitis C virus, human immunodeficiency virus, norovirus, human rotavirus, influenza virus, etc.

Likewise, cells include all of animal cells, plant cells and insect cells.

Nucleic acids include DNAs, RNAs, artificial nucleic acids, etc.

Polysaccharides include starch, glycogen, chitin, carrageenan, etc.

Proteins include antigens, antibodies, enzymes, dye proteins, peptides, polypeptides, hormones, receptors, allergens, etc.

Small molecules include nucleotides (e.g., nucleotide triphosphates or deoxynucleotide triphosphates), sugars (e.g., glucose or galactose), amino acids (e.g., glutamic acid or lysine), dyes (e.g., fluoroscein or ethidium bromide), hormones (e.g., epinephrine or peptide hormones or steroids), etc.

It should be noted that the above bio-related substances are listed for illustrative purposes and the bio-related substances intended in the present invention are not limited to these substances.

3. Assay Tube (1)

As described above, the bio-related substance assay tube of the present invention comprises a first microparticle on which a substance capable of binding to a target bio-related substance to be measured is immobilized, a second microparticle on which the above bio-related substance is immobilized in a given amount, and a third microparticle for use as a negative control in the tube. This configuration allows measurement of a target bio-related substance and compensation of this measured value at the same time in a single system, and further enables more accurate quantification in a simple manner. As a third embodiment directed to such a bio-related substance assay tube of the present invention, a bio-related substance assay tube further comprising light-shielding beads is shown in FIG. 5.

A bio-related substance assay tube 13 comprises, in its inner cavity, a target substance capture bead (first microparticle) 14 for detecting and quantifying a target bio-related substance (e.g., a protein) contained in an analyte, a negative control bead (third microparticle) 15, a compensation bead (second microparticle) 16, and light-shielding beads 17 interposed therebetween, wherein the light-shielding beads 17 do not transmit light. By comprising the light-shielding beads 17 having light-shielding properties, which are interposed to separate the target substance capture bead 14, the negative control bead 15 and the compensation bead 16, measurement and quantification of a self-emitting bead can be accomplished efficiently and accurately without encountering any interference with light emission from its adjacent beads.

Figure 5:
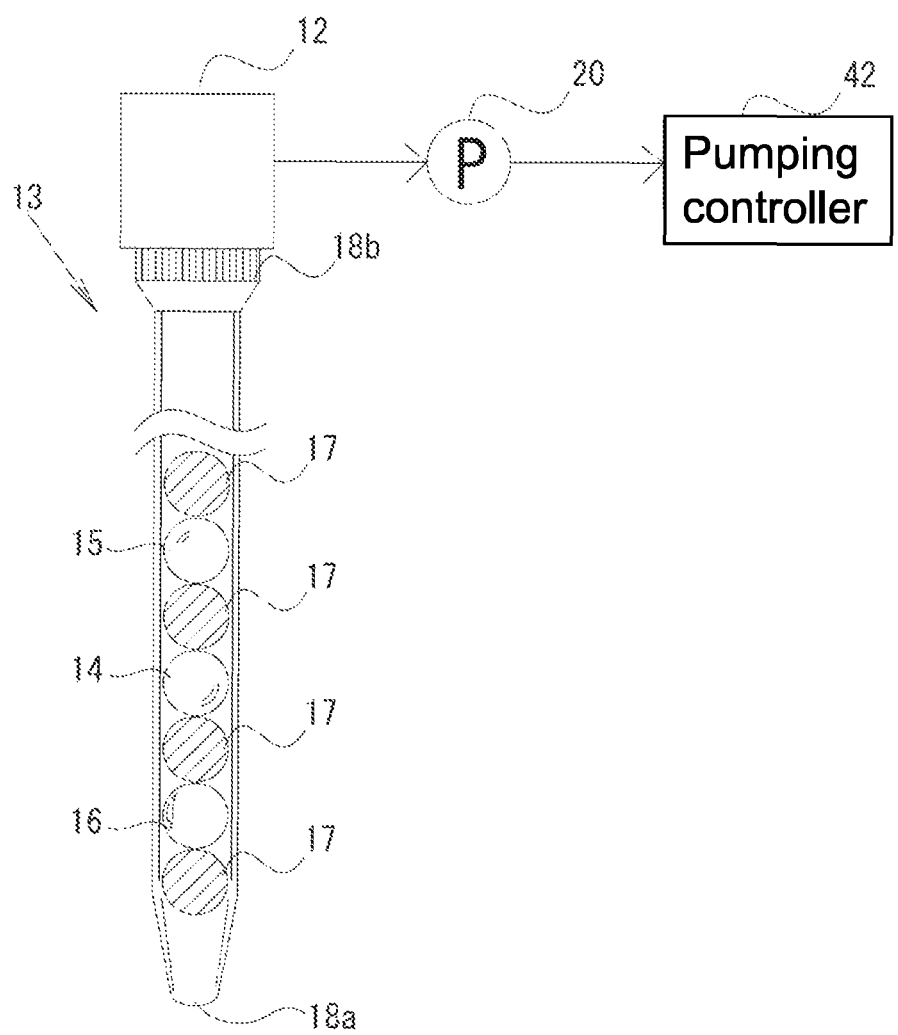
FIG. 5 schematically shows a bio-related substance assay tube comprising light-shielding beads.

The bio-related substance assay tube 13 shown in FIG. 5 is one embodiment of a tube comprising the above four types of beads, and is formed into a hollow cylinder which has an opening 18a on a tapered tip at one end and may also comprise an attachment 18b freely attachable to a mount unit 12 at the other end. In this case, the mount unit 12 has a nozzle (not shown) communicating with a pump whose driving is controlled by a pump controller, and the bio-related substance assay tube 13 is mounted in the mount unit 12 such that this nozzle and the inner cavity of the tube communicate with each other, whereby the tube can suck up a liquid into the tube and discharge the sucked liquid out of the tube.

4. Quantification System (1)

Next, an explanation will be given below of a quantification system comprising the bio-related substance assay tube 13 of the present invention described above (i.e., a quantification system using an assay tube of chemiluminescence intensity compensation type). The quantification system of the present invention comprises, in addition to the above bio-related substance assay tube 13, a detection unit for detecting signals emitted from each bead (microparticle) in this tube 13, a compensation unit for compensating data of the detected signals by referring to a previously prepared calibration curve, and an arithmetic unit for quantifying a bio-related substance based on the compensated data. An embodiment of this system will be explained below.

Figure 6:
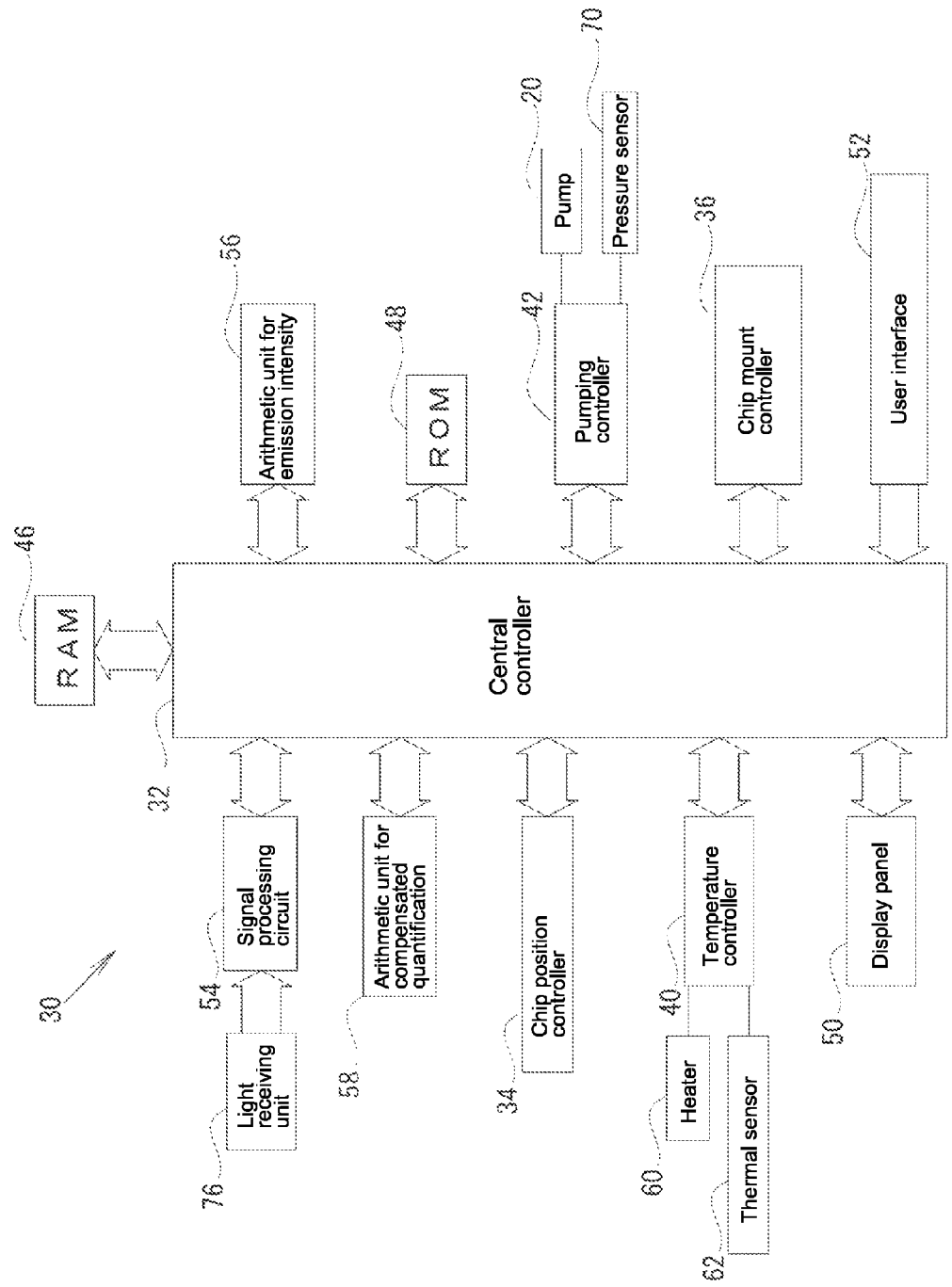
FIG. 6 is a functional block diagram of the quantification system of the present invention for emission intensity compensation.

In the quantification system of the present invention, for example, a series of operations covering quantification of a target bio-related substance contained in an analyte are automatically performed. A schematic functional block diagram of a quantification system comprising the above quantification tube is shown in FIG. 6.

A quantification system 30 has a central controller 32, a chip position controller 34, a chip mount controller 36, a temperature controller 40, a pumping controller 42, an RAM 46, a ROM 48, a display panel 50, a user interface 52, a signal processing circuit 54, an arithmetic unit for emission intensity 56, an arithmetic unit for compensated quantification 58, a timer (not shown) and so on, and further comprises the above bio-related substance assay tube 2, in a removable state, for detecting and quantifying a target bio-related substance.

The chip position controller 34 comprises mutually orthogonal XYZ axes and controls the position of a nozzle via a stepping motor or a servo-motor. The X and Y axes are almost parallel to a well plate and are orthogonal to each other, while the Z axis is almost vertical to the well plate. The nozzle may be moved in two steps, for example, by being moved on these X and Y axes almost parallel to the well plate and being moved on the Z axis almost vertical to the well plate.

The ROM 48 stores various control programs. Depending on the operating mode selected by a user through the user interface 52, a corresponding control program is unfolded from the ROM 48 into the RAM 46, and the central controller 32 controls each unit in the quantification system 30 on the basis of this control program unfolded in the RAM 46.

The display panel 50 shows the items required to be provided to a user. For example, items including the number of pumpings during sample (analyte) pretreatment, the flow rate during pumping, the suction and discharge volumes, and the moving speed of the bio-related substance assay tube 2 can be shown in the display panel 50 and can be confirmed by a user on the display panel. If various settings are desired to be changed, they can be changed through the user interface 52.

The timer, which is not shown, counts the time depending on the program read from the ROM 48. Time counting is performed, e.g., during incubation or pumping, and thereby ensures accurate implementation of each step.

The temperature controller 40 comprises a heater 60, a thermal sensor 62 and the like to control the temperature of a liquid held in the bio-related substance assay tube. The heater 62 generates heat by power supply from the temperature controller 40, while the thermal sensor 62 sends temperature signals to the temperature controller 40 depending on the temperature of a liquid held in the bio-related substance assay tube 2. The temperature controller 40 detects the temperature based on the temperature signals from the thermal sensor 62 and regulates power supply to the heater 60.

The chip mount controller 36 is provided for the purpose of mounting the bio-related substance assay tube 13 in the mount unit 12 and removing the bio-related substance assay tube 13 from the mount unit 12. The chip mount controller 36 is provided somewhat apart from a well plate in which wells each holding an analyte are arranged, so that contamination will not occur in case the liquid may splash from the bio-related substance assay tube 13 during replacement of the bio-related substance assay tube 2. The chip mount controller 36 comprises, for example, a holding unit for holding the bio-related substance assay tube 2 and a chip-providing unit for providing another new bio-related substance assay tube 13. If the nozzle moves up along the Z axis while holding the bio-related substance assay tube 13 by the holding unit, the bio-related substance assay tube 13 is removed from the nozzle. Then, the exposed nozzle is moved on the X and Y axes and reaches a position above a new bio-related substance assay tube 13. The chip-providing unit holds the new bio-related substance assay tube 13 with its mount unit up and its tip down, and when the nozzle moves down along the Z axis, the nozzle is attached to the mount unit of the new bio-related substance assay tube 13.

The pumping controller 42 comprises a pump 20 and a pressure sensor 70 to control suction and discharge of an analyte through the nozzle and the bio-related substance assay tube 13 mounted in this nozzle. The pump 20 comprises, for example, a cylindrically shaped housing and a piston movably fitted to this housing, as well as a motor for driving this piston, wherein the inside of the housing communicates with the opening of the nozzle. Movement of the piston is controlled, for example, by a servo-motor, while driving of the servo-motor is controlled by driving control signals from the pumping controller 42. Upon operation of the piston, a liquid can be sucked up or discharged through the opening of the nozzle.

In the opening of the nozzle, the pressure sensor 70 for detecting the pressure is provided, and the pressure sensor 70 sends pressure signals to the pumping controller 42. The pumping controller 42 monitors the pressure on the basis of the pressure signals from this pressure sensor 70. In such a configuration, for example, when the tip of the bio-related substance assay tube 13 is soaked in a sample within a well, the pressure detected by the pumping controller 42 exceeds a predetermined threshold, in response to which driving control signals are sent to the servo-motor. During both suction and discharge of an analyte, the pressure sensor 70 always sends pressure signals to the pumping controller 42, which allows the pumping controller 42 to control driving of the servo-motor with high accuracy for monitoring whether the pressure for suction or discharge of an analyte is too high or too low, whereby it is possible to control whether suction and discharge are performed within a predetermined range.

Figure 7:
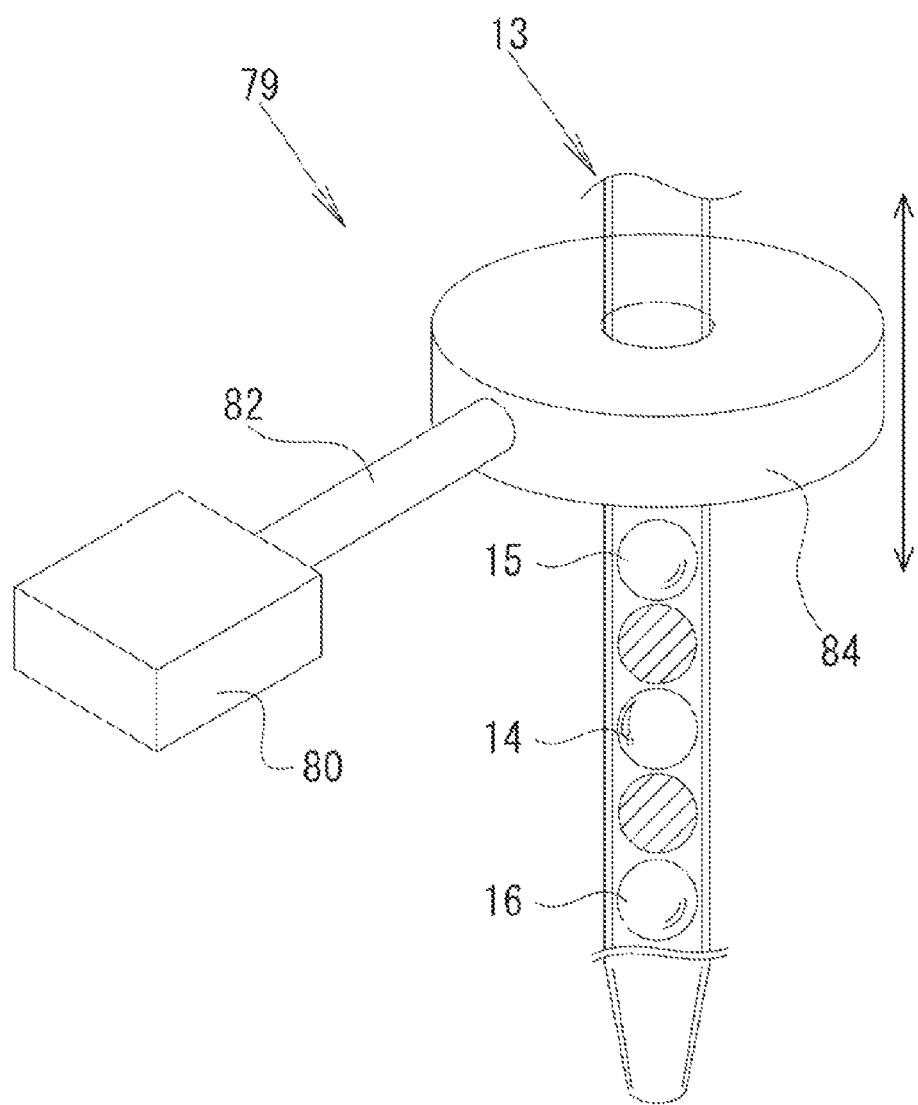
FIG. 7 is a perspective view showing a measurement system for reading emission intensity from each bead aligned in a bio-related substance assay tube.

The signal processing circuit 54 processes light receiving signals from a light receiving unit 76 to form, e.g., binary light receiving data. The light receiving unit 76 may comprise, for example, a PMT (photomultiplier) or an image sensor such as a CCD image sensor, a CMOS image sensor, etc. An example of a configuration where a PMT is used in the light receiving unit 76 is shown in FIG. 7. As shown in FIG. 7, a measurement system for emission intensity 79 comprises a PMT 80, a POF (plastic optical fiber) 82, a ring member 84 and so on. The light (signals) from each bead is guided through the POF 82, and the PMT 80 outputs light receiving signals upon receiving the light from the POF 82. The PMT 80, POF 82 and ring member 84 move along the longitudinal direction of the bio-related substance assay tube 13, and the PMT 80 outputs light receiving signals in response to the emission intensity of each bead.

The signal processing circuit 54 comprises a sampling circuit, an amplifier, an A/D converter and so on (all of which are not shown) to amplify and digitize the light receiving signals sent from the light receiving unit 76, thereby forming light receiving data. The light receiving data thus formed is sent from the signal processing circuit 54 to the arithmetic unit for emission intensity 56. When emission intensity is read, for example, in the direction from the opening to the attachment of the assay tube 13, light receiving data formed in response to the light from the negative control bead 15, the target substance capture bead 14 and the compensation bead 16 are sent from the light receiving unit 76.

The arithmetic unit for emission intensity 56 reads an emission intensity calculation program stored, e.g., in the RAM 46, and calculates emission intensity according to this program, based on the light receiving data from the signal processing circuit 54. For example, the emission intensity is calculated by receiving, from the signal processing circuit 54, the light receiving data corresponding to the light from the negative control bead 16, the target substance capture bead 14 and the compensation bead 16 aligned in the bio-related substance assay tube 2. The emission intensity data calculated in response to the light from the compensation bead 16 and the emission intensity data calculated in response to the light from the target substance capture bead 14 are sent to the arithmetic unit for compensated quantification 58, while the emission intensity data corresponding to the light from the negative control bead 16 is sent to the central controller 32. These data are used for assay. In this assay, for example, it is determined whether the emission intensity corresponding to the light from the negative control bead 16 is smaller than the emission intensity calculated in response to the light from the target substance capture bead 14. As a result, if the emission intensity is determined to be abnormal, a warning sign is shown in the display panel 50.

Figure 8:
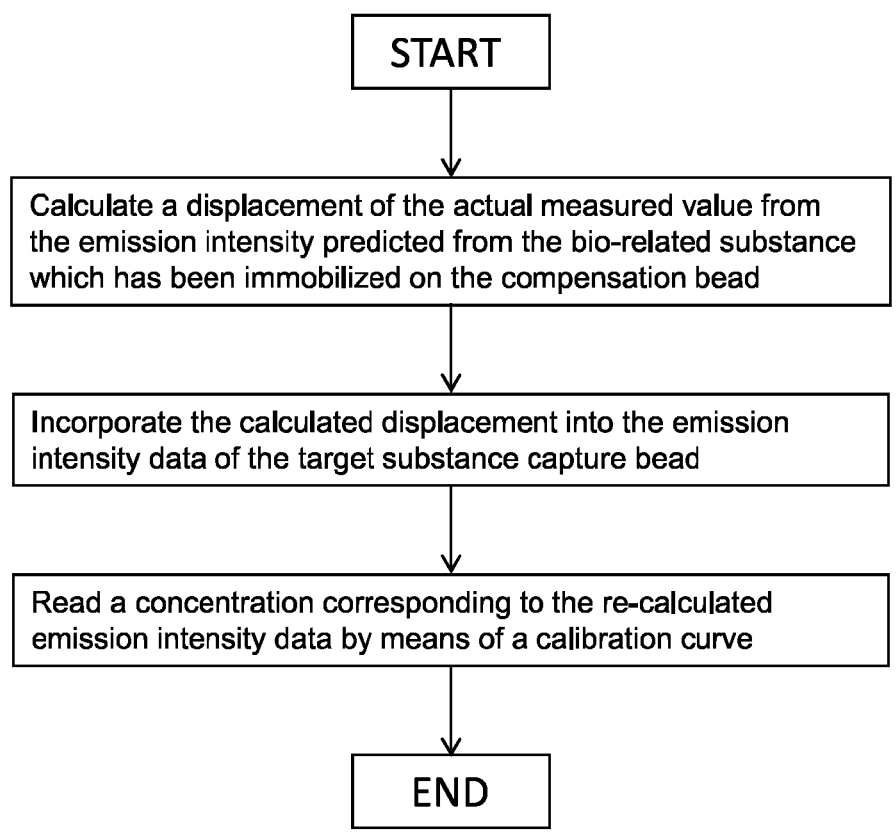
FIG. 8 is a flow chart showing procedures for quantification of a target substance bound to a target substance capture bead.

The arithmetic unit for compensated quantification 58 quantifies a target bio-related substance based on the emission intensity data corresponding to the light from the target substance capture bead 14 and the emission intensity data corresponding to the light from the compensation bead 16. In quantification of a bio-related substance, procedures for quantification of a target bio-related substance are as follows as shown in FIG. 8. (1) Calculate a displacement Δ of the actual measured value from the emission intensity predicted from the bio-related substance which has been immobilized on the compensation bead 16. (2) Incorporate the calculated displacement Δ into the emission intensity data of the target substance capture bead 14. (3) Read a concentration corresponding to the re-calculated emission intensity data by means of a calibration curve. The foregoing procedures ensure more accuracy of the value quantified for the bio-related substance captured by the target substance capture bead 14.

Figure 9:
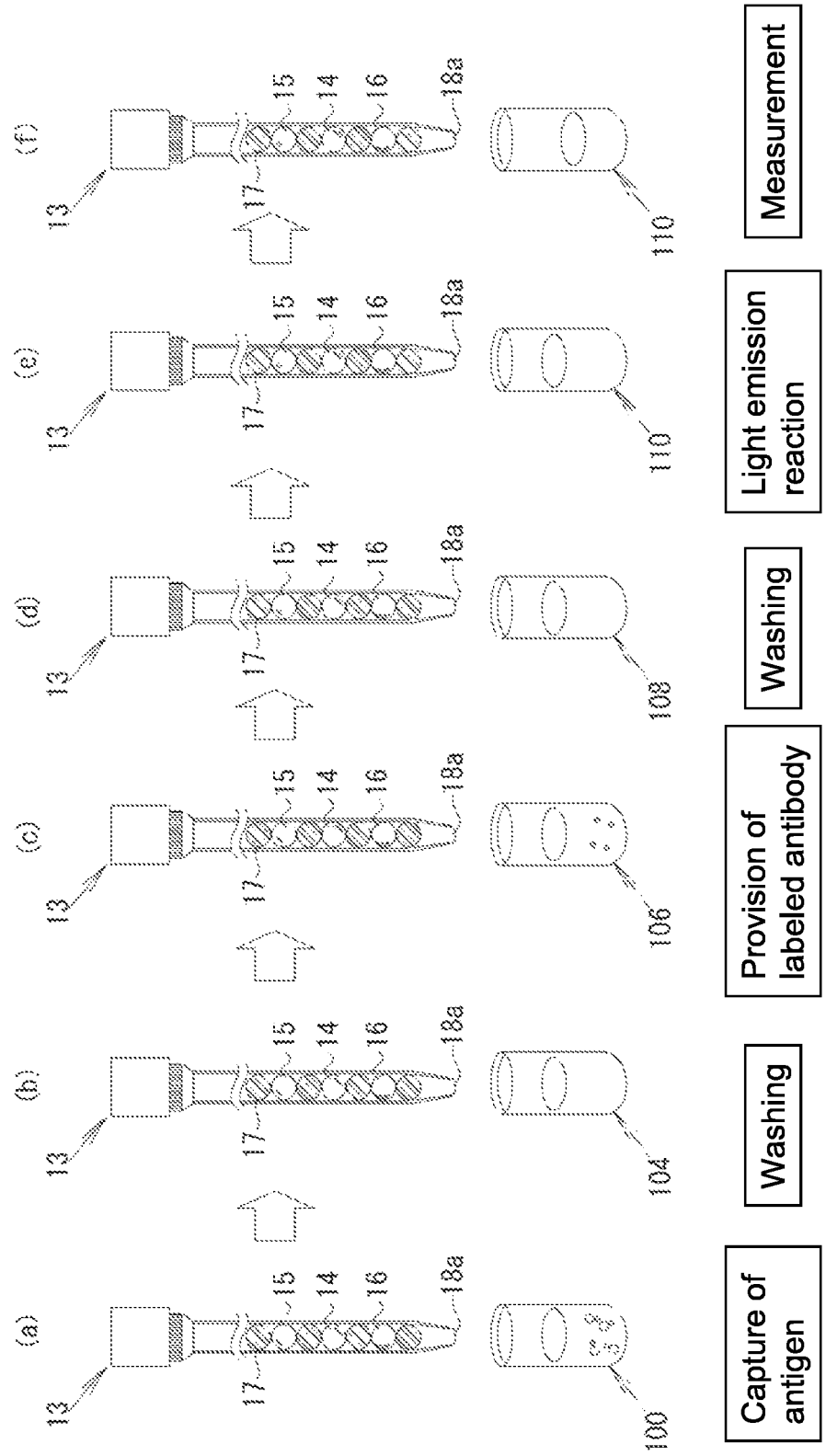
FIG. 9 briefly illustrates the effect of the present invention by taking antigen-antibody reaction as an example.

Next, antigen assay based on antibody-antigen reaction is given as an example to describe the effect of the present invention. As shown in FIG. 9, a cylindrically shaped transparent bio-related substance assay tube 13 comprises a target substance capture bead 14 on which antibodies against antigens have been immobilized, a compensation bead 15, and a negative control bead 16. Light-shielding beads 17 are interposed to separate the target substance capture bead 14, the negative control bead 15 and the compensation bead 16, and the individual beads 15 to 17 are aligned along the longitudinal direction of the bio-related substance assay tube 13.

As shown in FIG. 9(*a*), once the opening 18*a* of the bio-related substance assay tube 13 is soaked in a well 100 containing a sample solution to suck up the sample solution in the well 100 into the bio-related substance assay tube 13, antigens bind to their respective antibodies immobilized on the target substance capture bead 14 and are captured on the target substance capture bead 14. Suction and discharge of the analyte are repeated given times to thereby ensure binding of the antigens to the antibodies on the target substance capture bead 14.

As shown in FIG. 9(*b*), after pumping the analyte, a washing solution in another well 104 is sucked up to wash the target substance capture bead 14. Analyte components other than the antigens bound via antigen-antibody reaction are removed by washing. As shown in FIG. 9(*c*), after washing the target substance capture bead 14, the opening 18*a* of the bio-related substance assay tube 13 is soaked in an enzyme-labeled antibody solution in another well 106 to suck up the enzyme-labeled antibody solution into the bio-related substance assay tube 13. As shown in FIG. 9(*d*), after the enzyme-labeled antibody solution is repeatedly pumped given times, a washing solution in another well 108 is pumped to remove excess of the enzyme-labeled antibody solution, thereby washing the target substance capture bead 14 on which the antigens and the enzyme-labeled antibodies are bound. As shown in FIG. 9(e), after washing, the bio-related substance assay tube 13 is controlled to move to a well 110 containing a substrate solution for light emission to thereby initiate the detection step.

The opening 18a of the bio-related substance assay tube 13 is soaked in the well 110 containing a substrate solution for light emission to suck up the substrate solution into the bio-related substance assay tube 13. The substrate solution is repeatedly pumped given times to ensure sufficient reaction.

A light irradiation unit, which is not shown, and the light receiving unit 76 are controlled for their movement such that they face to each other across each bead, whereby the light beam from the light irradiation unit is received by the light receiving unit 76 across each bead in the bio-related substance assay tube 13. In response to light receiving signals sent from the light receiving unit 76, the signal processing circuit 54 sends light receiving data based on the light receiving signals from the light receiving unit 76 to the arithmetic unit for emission intensity 56. The arithmetic unit for emission intensity 56 calculates emission intensity based on the received data to send emission intensity data to the arithmetic unit for compensated quantification 58. The arithmetic unit for compensated quantification 58 compensates the emission intensity of the target substance capture bead 14 on the basis of the emission intensity data from the compensation bead 15. It should be noted that it is preferred to use light-shielding beads if a target bio-related substance is quantified through light emission reaction, In view of the foregoing, by using the bio-related substance assay tube and quantification system of the present invention, quantification of a target bio-related substance can be performed in a single system and compensation of the measured value can be conducted in the same environment. Moreover, fixed conditions can be used in pumping between the bio-related substance assay tube and each well, and vortexing, reaction, washing, measurement and other steps can be conducted under the same conditions, thus ensuring less biased measurement. In addition, by aligning the target substance capture bead, the compensation bead and the negative control bead in a single bio-related substance assay tube, multiple reactions can be simultaneously performed and hence a highly convenient quantification system can be provided.

It should be noted that in the above embodiment, the numbers of target substance capture beads, compensation beads and negative control beads are each set to one, although two or more beads may be used for each purpose. When two or more beads are used for each purpose and their averages are used in quantification of a target substance or the like, more reliable quantification can be expected.

5. Assay Tube (2)

The bio-related substance assay tube of the present invention achieves preparation of a calibration curve and quantification of a target substance at the same time. When preparation of a calibration curve and quantification of a target bio-related substance are performed at the same time, more preferred conditions are possible for quantification. An explanation will be given below of a second embodiment where a bio-related substance is quantified using the quantification procedure (ii) which is intended to quantify a target bio-related substance while preparing a calibration curve.

Figure 10:
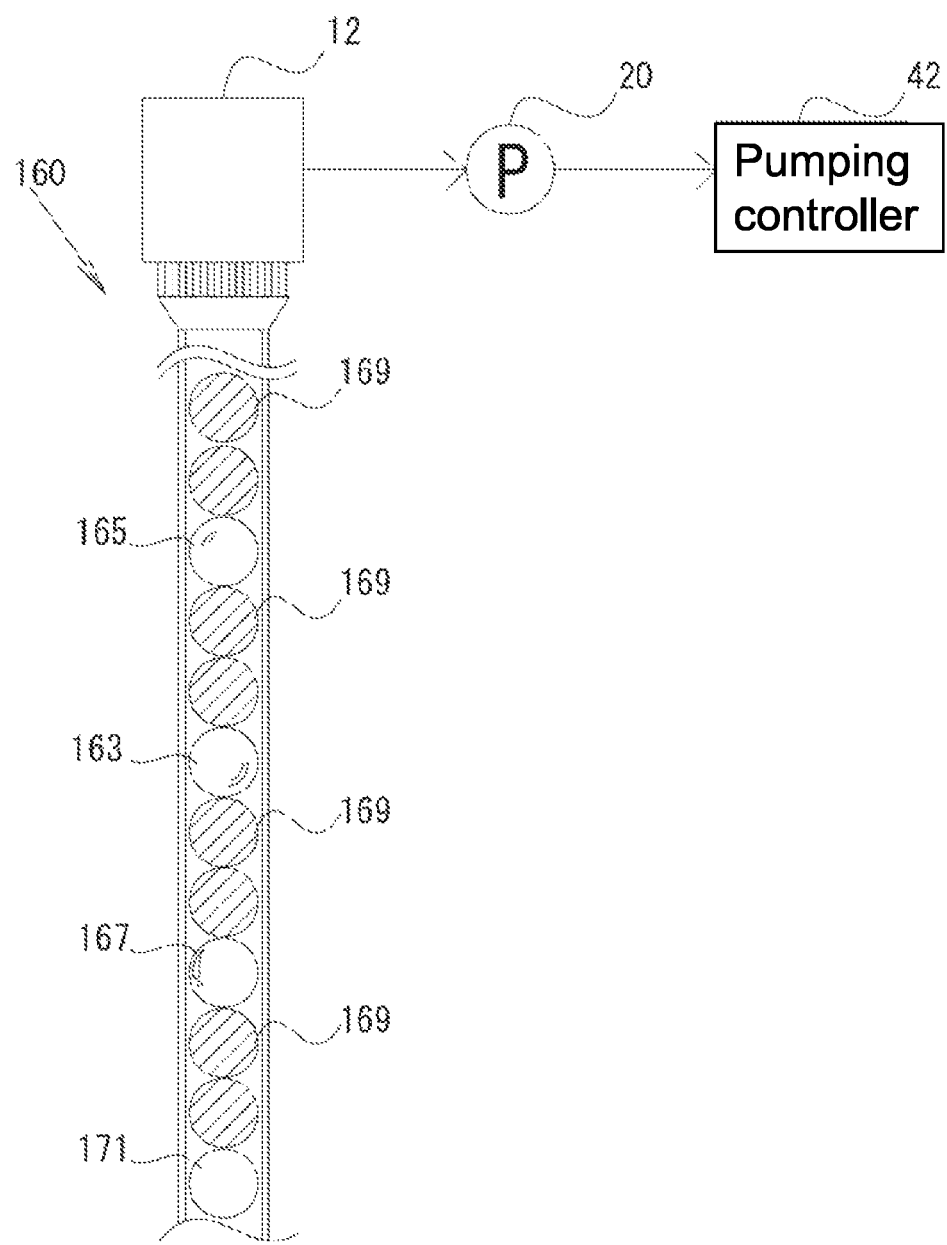
FIG. 10 schematically shows a bio-related substance assay tube comprising a plurality of beads carrying different amounts of antibody immobilized thereon for the purpose of preparing a calibration curve.

An example of an assay tube which allows preparation of a calibration curve and quantification of a target bio-related substance at a time is shown in FIG. 10.

For preparation of a calibration curve, the bio-related substance assay tube comprises a plurality of microparticles on which different amounts of a bio-related substance have been immobilized, and a calibration curve is prepared based on emission intensity data of these second microparticles on which different amounts of the bio-related substance have been immobilized. As shown in FIG. 10, the bio-related substance assay tube 160 has a target substance capture bead (first microparticle) 163 capable of binding to a target substance (e.g., a protein), first and second standard beads (second microparticles) 165 and 167 on which different amounts of the target substance have been immobilized, and a blank bead (third microparticle) 171. The target substance capture bead 163, the first and second standard beads 165 and 167, and the blank bead 171 are aligned via light-shielding beads 169. The emission intensity of these first and second standard beads 165 and 167 and the amounts of the bio-related substance immobilized thereon may be used to prepare a calibration curve. Using the calibration curve thus prepared, the amount of the target bio-related substance can be calculated based on the emission intensity of the target substance capture bead 163. It should be noted that the number of standard beads is not limited to two and may be three or more.

6. Quantification System (2)

Figure 11:
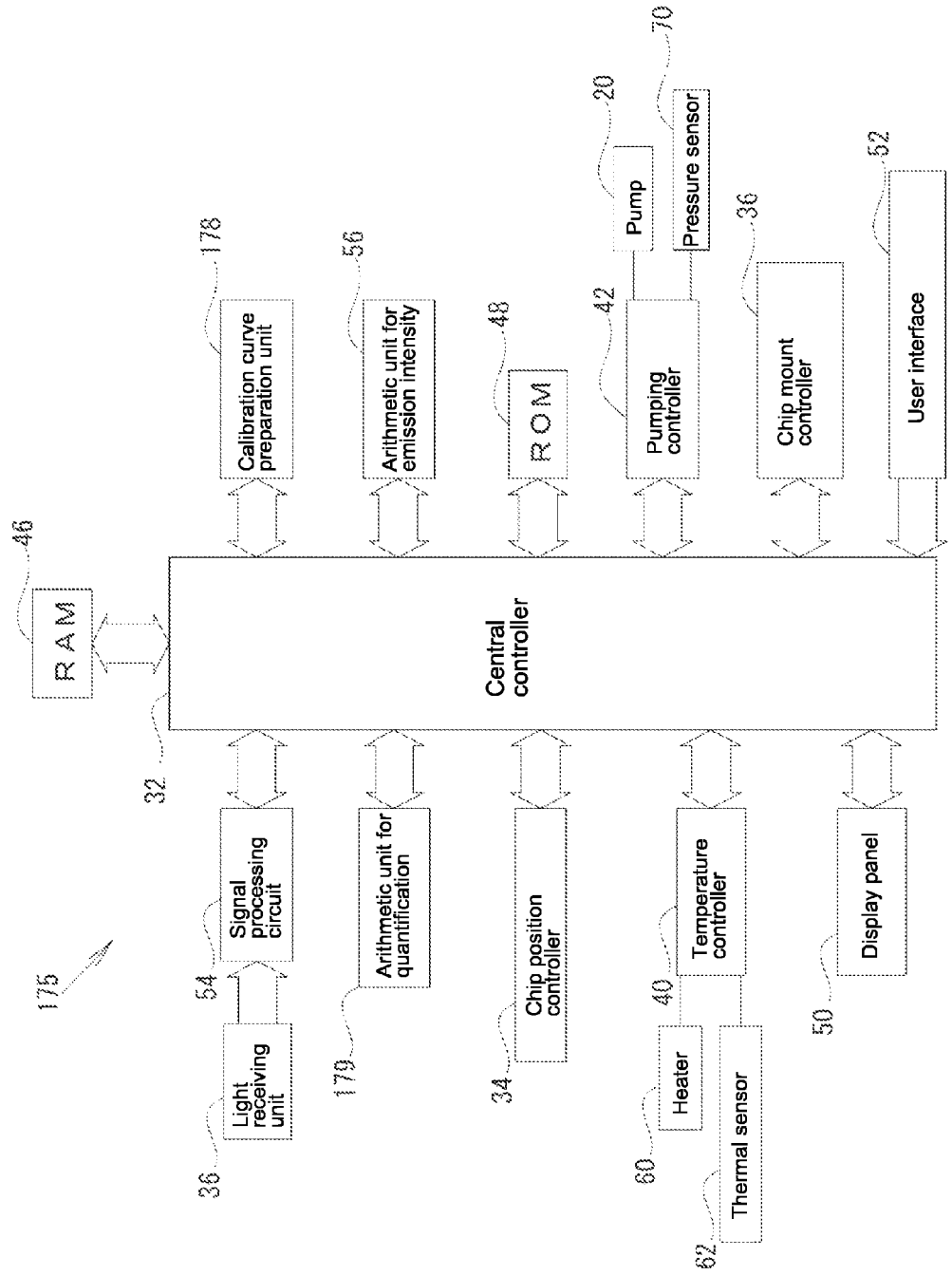
FIG. 11 is a functional block diagram of a quantification system for quantifying a target substance using a bio-related substance assay tube comprising a plurality of beads carrying different amounts of antibody immobilized thereon.

A brief explanation will be given below of a quantification system comprising the above bio-related substance assay tube 160. The second quantification system of the present invention comprises a bio-related substance assay tube, a detection unit for detecting signals emitted from microparticles in this tube, a calibration curve preparation unit for preparing a calibration curve based on the detected signals, and an arithmetic unit for quantifying a bio-related substance by referring to the prepared calibration curve. A functional block diagram of such a quantification system is shown in FIG. 11. It should be noted that the same configurations as found in the block diagram in FIG. 6 are indicated with the same reference numerals as in FIG. 6 and their explanation is omitted.

A quantification system 175 comprises a calibration curve preparation unit 178 and an arithmetic unit for quantification 179. An arithmetic unit for emission intensity 56 calculates first and second emission intensity data based on light receiving signals from the first and second standard beads 165 and 167 and send these data to the calibration curve preparation unit 178. The calibration curve preparation unit 178 prepares a calibration curve by calculation based on the first and second emission intensity data, and the resulting calibration curve is stored in an RAM 46. Based on the emission intensity of the target substance capture bead 163, the arithmetic unit for quantification 179 calculates a corresponding concentration value by referring to the calibration curve stored in the RAM 46.

In this way, in the quantification system 175, the point X on the graph (see FIG. 4) is plotted from the emission intensity and known concentration of the first standard bead 165, while the point Y on the graph is also plotted from the emission intensity and known concentration of the second standard bead 167, whereby a calibration curve is prepared. The calibration curve thus prepared is used to quantify the concentration E of a target bio-related substance. The quantification system of the present invention allows these steps almost at the same time in a single system and hence enables highly accurate quantification.

It should be noted that although spherical light-shielding beads are used in the above first and second embodiments, light-shielding members to be interposed between individual beads are not limited to light-shielding beads and may be any members as long as they have light-shielding functions.

Figure 12:
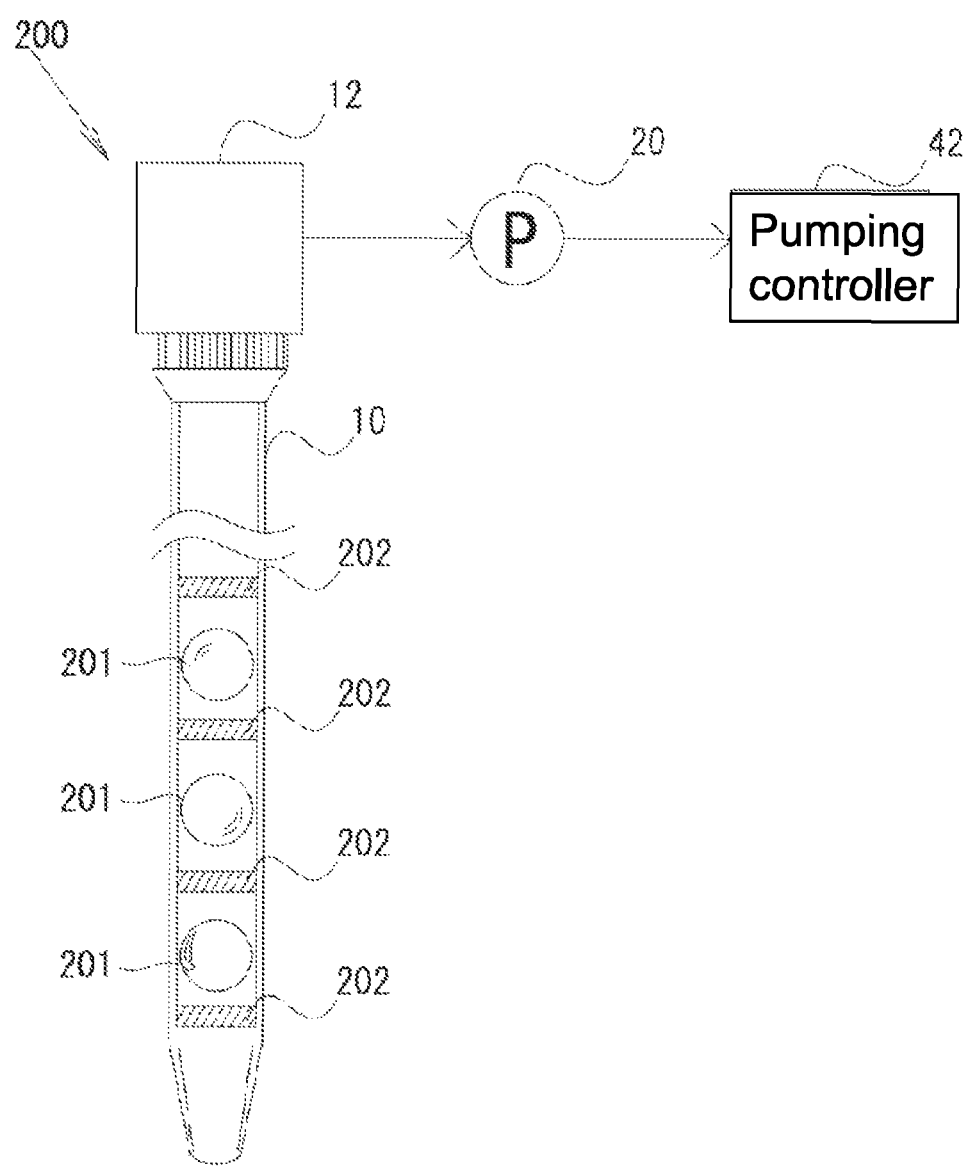
FIG. 12 schematically shows a bio-related substance assay tube comprising light-shielding filters interposed between individual beads.

For example, as shown in FIG. 12, light-shielding filters 202 may be interposed between individual beads 201.

Moreover, when a plurality of bead sets are used as microparticles, multiple bio-related substances can be compensated and quantified at the same time. For example, a first bead set comprising a target substance capture bead for capturing a first target substance, a compensation bead and a negative control bead, as well as a second bead set comprising a target substance-binding bead for capturing a second target substance, a compensation bead and a negative control bead a re prepared. These first and second bead sets may be, for example, colored and set in place for measurement in the bio-related substance assay tube to conduct formation and compensation of the measured data, and calculation of a quantified value for each bead set. In this way, a unique bead is adapted to each target bio-related substance and confirmed for its position, whereby measurement and quantification can be performed for each bead. This simultaneously allows compensation and quantification on the measured values of multiple bio-related substances, and hence enables the provision of a more convenient bio-related substance assay tube or quantification system.

In addition to the quantification system using the assay tube comprising a first microparticle for capturing a bio-related substance, a second microparticle for preparing a calibration curve and a third microparticle for use as a negative control (e.g., FIGS. 10 and 11), the present invention can also provide a measurement system using an assay tube comprising, as another second microparticle, a microparticle for compensation of errors (e.g., measurement errors due to differences in the lot or serial number of assay tubes, errors due to differences in the model name or model number of quantification systems, errors due to differences in the type of reagents used for quantification). The use of such an assay tube can be expected to further improve quantification accuracy in systems for quantifying a target bio-related substance. An example of a system using such an assay tube will be explained by referring to FIGS. 13 and 14. It should be noted that the same configurations as found in the above first embodiment are indicated with the same reference numerals and their explanation is omitted.

Figure 13:
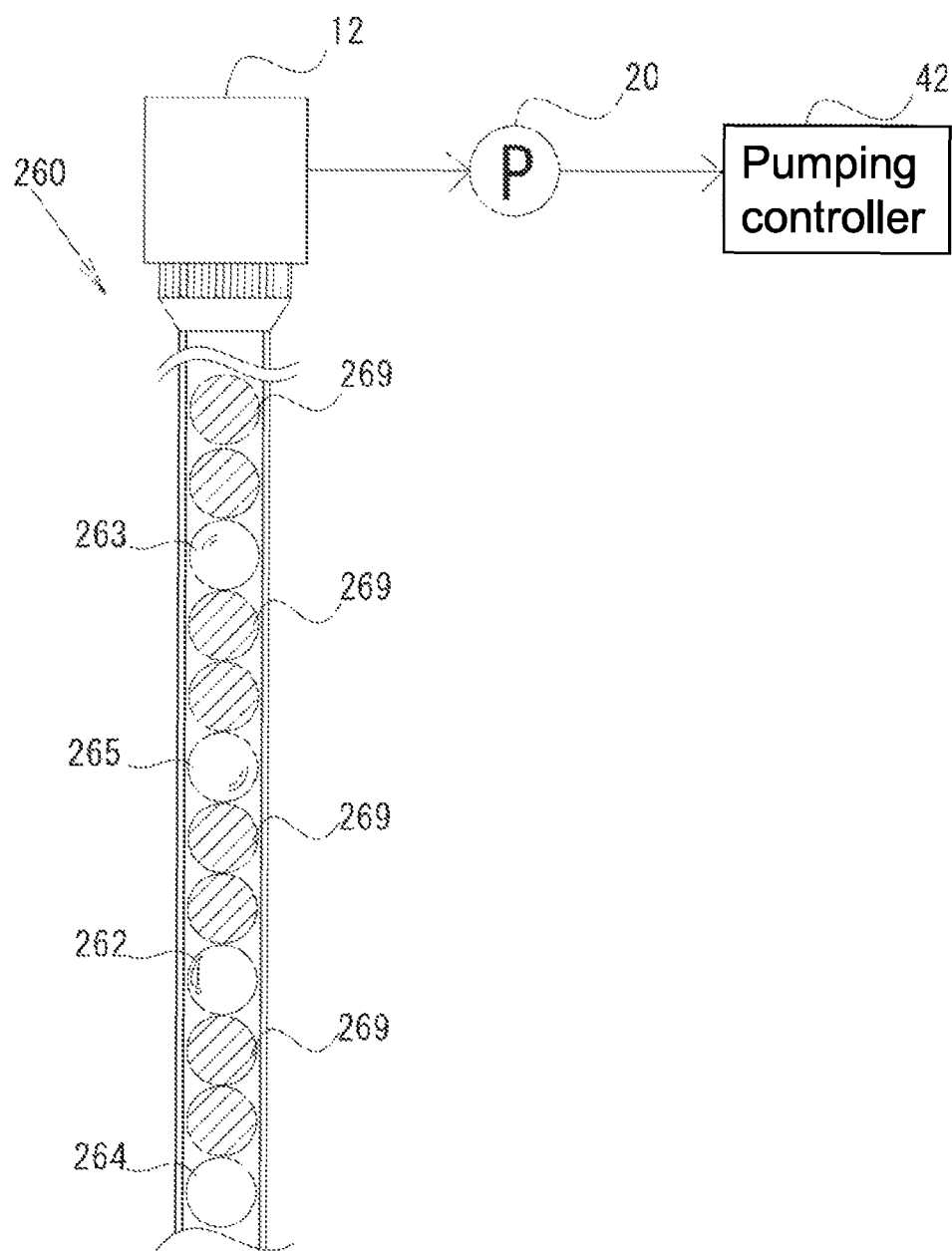
FIG. 13 schematically shows an assay tube comprising two types of second microbeads, i.e., a microparticle for compensation of errors (e.g., measurement errors due to differences in the lot or serial number of assay tubes, errors due to differences in the model name or model number of quantification systems, errors due to differences in the type of reagents used for quantification) and a microparticle for use as a positive control.
Figure 14:
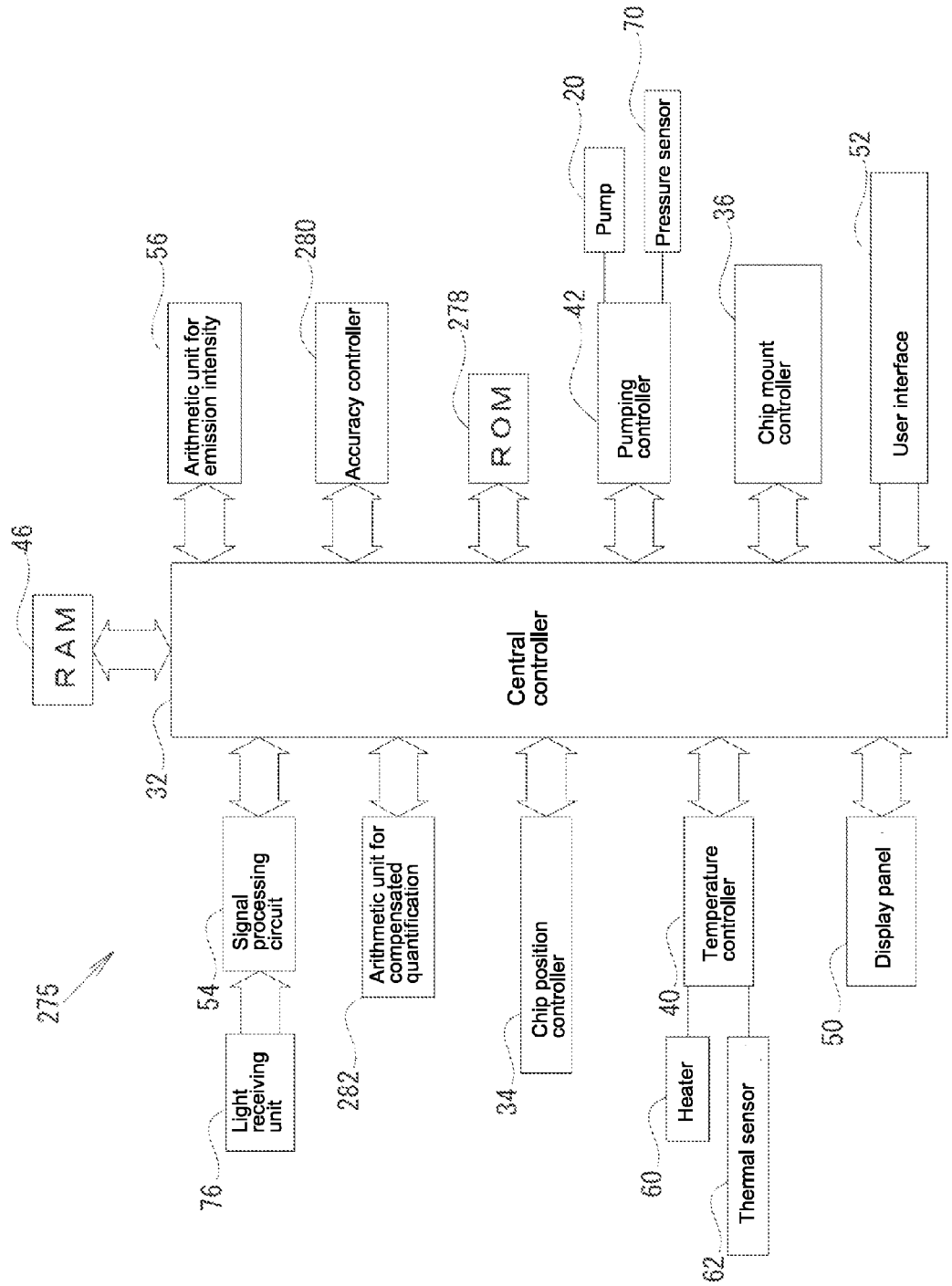
FIG. 14 is a functional block diagram of a quantification system for quantifying a target bio-related substance using an assay tube comprising two types of second microbeads, i.e., a microparticle for compensation of errors (e.g., measurement errors due to differences in the lot or serial number of assay tubes, errors due to differences in the model name or model number of quantification systems, errors due to differences in the type of reagents used for quantification) and a microparticle for use as a positive control.

An example of an assay tube comprising two types of second microparticles, i.e., a microparticle for use as a positive control and a microparticle for compensation purposes is shown in FIG. 13. An assay tube 260 comprises a first bead (first microparticle) 262 for capturing a target bio-related substance, a second bead (second microparticle) 263 for use as a positive control, a third bead (third microparticle) 264 for use as a negative control, and a fourth bead (second microparticle) 265 for emission intensity compensation. It is preferred that light-shielding beads 269 are interposed to separate these first to fourth beads 262 to 265 such that they are aligned in a line in the inner cavity of the assay tube 260.

If a quantification system 275 (see FIG. 14) is given as an example of a quantification system using such microparticles, an analyte is introduced into the assay tube 260 mounted in this system and a labeling solution is then introduced into the assay tube 260. Into the assay tube 260 receiving the labeling solution, a substrate solution is further introduced to cause chemiluminescence.

Light emitted from each of the beads 262 to 265 is received, for example, by a light receiving unit 76 (e.g., a PMT), and the light receiving unit 76 outputs light receiving signals. An arithmetic unit for emission intensity 56 calculates the emission intensity of the beads 262 to 265 on the basis of light receiving data from a signal processing circuit 54.

An accuracy controller 280 calculates a difference in emission intensity between the second bead 263 for use as a positive control and the third bead 264 for use as a negative control.

Moreover, reference emission intensity used for accuracy control is stored in a ROM 278, and the accuracy controller 280 performs a comparison between the emission intensity of the fourth bead 265 calculated in the arithmetic unit for emission intensity 56 and the reference emission intensity stored in the ROM 278 to thereby calculate, for example, a difference in their emission intensity.

An arithmetic unit for compensated quantification 282 selects and reads an appropriate compensation program from among a plurality of compensation programs stored in the ROM 278, for example, on the basis of the above difference in emission intensity between the second bead 263 and the third bead 264, as well as the above difference in emission intensity between the reference emission intensity and the fourth bead 265.

Based on the compensation program thus read, the arithmetic unit for compensated quantification 282 compensates the emission intensity of the first bead 262, and the compensated emission intensity value is checked against a calibration curve to quantify a target bio-related substance.

In view of the foregoing, by using the second bead for use as a positive control, the third bead for use as a negative control and the fourth bead for compensation purposes, a target bio-related substance can be quantified more accurately while saving the effort required for correction of the system even when there are differences in the lot number or serial number of assay tubes, the model name or model number of quantification systems, and the type of reagents used for quantification, etc. In this way, the assay tube and quantification system of the present invention allow not only qualitative detection of the presence or absence of a target bio-related substance, but also quantification of the amount of the target bio-related substance, and hence enable the provision of a more convenient quantification system.

Moreover, the present invention can save the effort required for service and maintenance of the system and can be fully adapted to perform point-of-care testing for rapid diagnosis in the vicinity of a patient.

7. Quantification of Multiple Bio-Related Substances

Although the assay tubes and quantification systems designed to quantify a single bio-related substance have been described above, assay tubes and quantification systems may be configured to quantify multiple bio-related substances.

An explanation will be given below of an assay tube and a quantification system, which are designed to quantify multiple bio-related substances based on chemiluminescence from first to third microparticles. As an approach to quantify multiple bio-related substances, two measurement systems, i.e., first and second measurement systems are used here. In a case where mutually independent first and second measurement systems are used to quantify multiple bio-related substances, a means serving as a standard is required to link the first and second measurement systems. Such a standard may be, for example, microparticles used in common in the first and second measurement systems. Such microparticles used as a standard may be, for example, reference microparticles on which a substance is immobilized at known concentrations, and when an assay tube is provided with these reference microparticles, the emission intensity values measured in both first and second measurement systems can be linked to each other.

Figure 15:
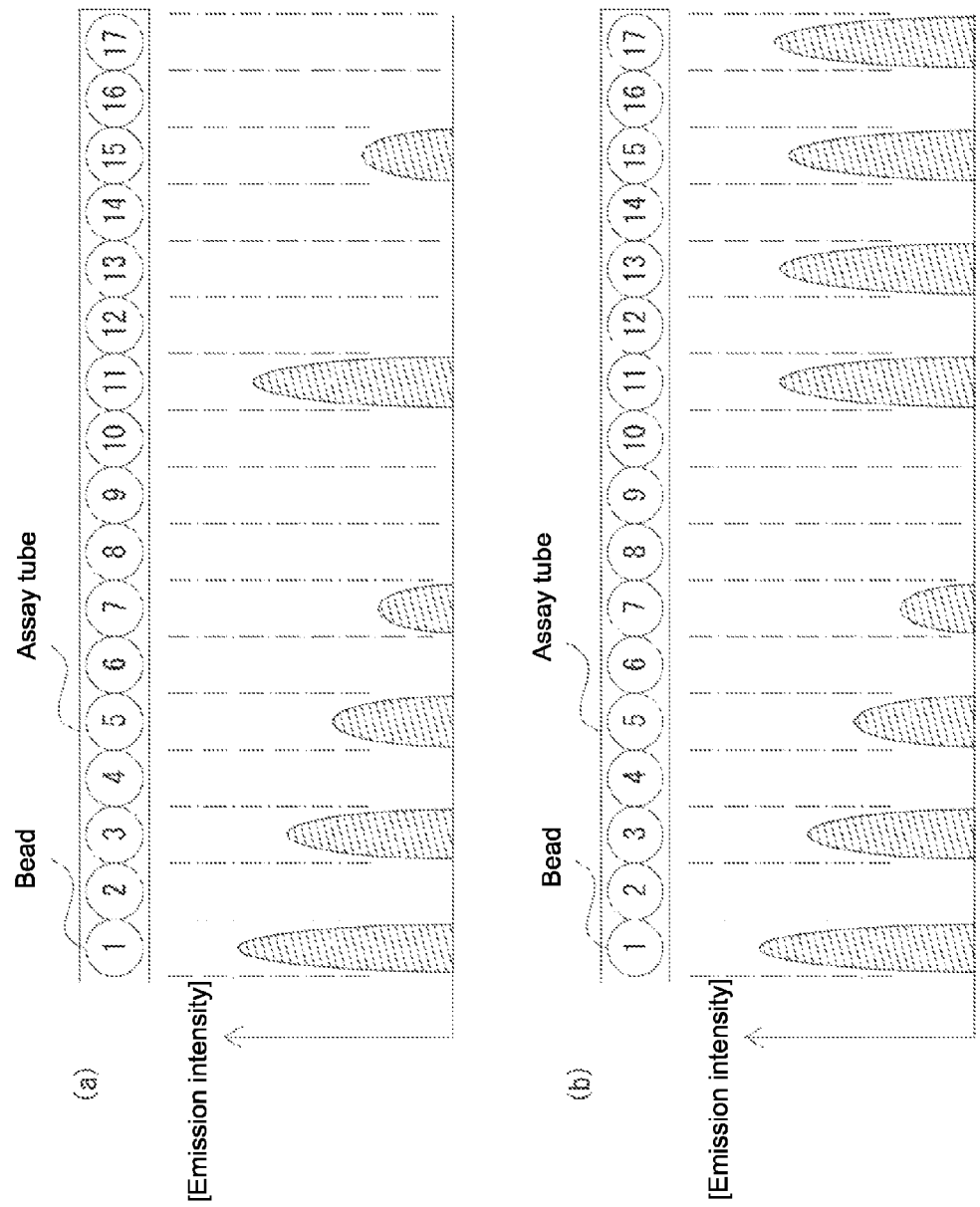
FIG. 15 illustrates an embodiment where two measurement systems are used to quantify multiple bio-related substances.

An example of an assay tube comprising reference microparticles is shown in FIG. 15. As shown in FIG. 15(*a*), an assay tube for use in the first measurement system comprises reference beads (reference microparticles) represented by bead Nos. 1, 3, 5 and 7, as well as a plurality of first beads (first microparticles; bead Nos. 11, 13, 15 and 17) for measuring target bio-related substances. Examples of reference microparticles include biotinylated protein-coated beads, and the reference microparticles are pre-treated, for example, such that a known substance is immobilized at gradually different concentrations. Examples of first beads for capturing multiple bio-related substances include anti-allergen antibody-coated beads. Four first beads are shown in the figure, whereby four bio-related substances can be quantified. However, the number of first beads is not limited to four, and may be less than four or may be five or more.

As shown in FIG. 15(*b*), an assay tube for use in the second measurement system comprises the same reference beads (bead Nos. 1, 3, 5 and 7) as used in the first measurement system, as well as second beads for use as a positive control (second microparticles; bead Nos. 11, 13, 15 and 17) which are prepared for the four bio-related substances to be quantified in the first measurement system.

On the second beads, for example, the target bio-related substances of known concentration are immobilized, whereby the second beads serve as a positive control for the target bio-related substances captured by the first beads. Bead No. 9 may be a blank bead serving as a third microparticle, and the even-numbered beads in the figure represent light-shielding microparticles.

In this way, the assay tubes used in the first and second measurement systems comprise common reference beads, and the emission intensity in the first measurement system and the emission intensity in the second measurement system can be linked through the emission intensity of these reference beads. As a result, if the reference beads produce equal emission intensity in the first and second measurement systems, quantified values can be calculated without compensating emission intensity values.

In a case where each bio-related substance is quantified based on its emission intensity, for example, each emission intensity is checked against a calibration curve for each bio-related substance read from a memory to thereby quantify each bio-related substance, as in the case of quantification for a single bio-related substance.

As described above, a plurality of measurement systems m ay be used to quantify multiple bio-related substances.

Although proteins or antigens are illustrated as target bio-related substances to be quantified in the above embodiment, bio-related substances are not limited thereto and may be, for example, peptides, hormones, receptors, nucleic acids, polysaccharides, enzymes, toxins, pathogens, cells, bacteria, viruses, microorganisms, allergens, parasites or the like, as described above.

8. Fluorescence-Based Quantification System

In the present invention, a target bio-related substance can be quantified by capturing the target bio-related substance by a sample capture bead serving as a first microparticle, soaking the sample capture bead in a substrate solution containing light emission reagents to cause light emission from a label on the sample capture bead, and measuring the intensity of this light emission. In addition to this chemiluminescence-based quantification system, the present invention also allows quantification of a target bio-related substance by detecting fluorescence from each microparticle.

An explanation will be given below of an embodiment of the present invention where a target bio-related substance is quantified by means of fluorescence.

In the present invention, a fluorescent dye may be directly or indirectly attached to a target bio-related substance, and this fluorescent dye may be irradiated with excitation light of a specific wavelength to thereby cause fluorescence emission from the target bio-related substance. A quantification system for a bio-related substance by means of such a fluorescent dye may comprise, for example:

a labeling means, by which fluorescent labels are provided to:
  a first microparticle capable of binding to a target bio-related substance;
  a second microparticle on which a given amount of the target bio-related substance has been immobilized; and
  a third microparticle which serves as a negative control;
a fluorescence intensity detection means, by which the fluorescently labeled first to third microparticles are irradiated with excitation light to detect fluorescence intensity; and
an arithmetic means, by which the fluorescence intensity detected by the fluorescence intensity detection means is checked against a calibration curve prepared for calculating the amount of the bio-related substance from the fluorescence intensity to thereby quantify the target bio-related substance.

In this quantification system, quantification of the bio-related substance bound to the first microparticle is accomplished based on a calibration curve. This calibration curve is preferably prepared before measurement of the bio-related substance or during measurement of the target bio-related substance.

Thus, a calibration curve used for calculating the amount of a bio-related substance based on its fluorescence intensity may be prepared and stored in a memory element (e.g., a memory) before quantification of the bio-related substance bound to the first microparticle, or may be prepared by measuring the fluorescence intensity of a plurality of second microparticles, on which different amounts of the bio-related substance have been immobilized, during measurement of the bio-related substance bound to the first microparticle.

In a case where a calibration curve is prepared and stored in a memory element before quantification of the bio-related substance bound to the first microparticle, it is preferred that the fluorescence intensity of the first microparticle is corrected based on the fluorescence intensity values of the second and third microparticles. On the other hand, in a case where a calibration curve is prepared from the fluorescence intensity of a plurality of second microparticles, on which different amounts of the bio-related substance have been immobilized, during measurement of the bio-related substance bound to the first microparticle, it is preferred that the calibration curve is prepared by also referring to the fluorescence intensity value of the third microparticle.

Examples of the third microparticle which serves as a negative control include a microparticle (blank particle) on which no target bio-related substance is immobilized. By using such a particle, background noise during measurement of a target bio-related substance can be detected, which allows compensation of the measured intensity, correction of a previously prepared calibration curve, or preparation of a calibration curve.

In this system, the first to third microparticles aligned in the assay tube are irradiated with excitation light to detect their fluorescence intensity. A single or multiple assay tubes may be used at the same time. This quantification system also comprises a nozzle for mounting an assay tube, and when a bio-related substance is quantified for multiple analytes, the assay tube is preferably replaced with a new one for every analyte.

The quantification system of the present invention will be described in more detail below.

Figure 16:
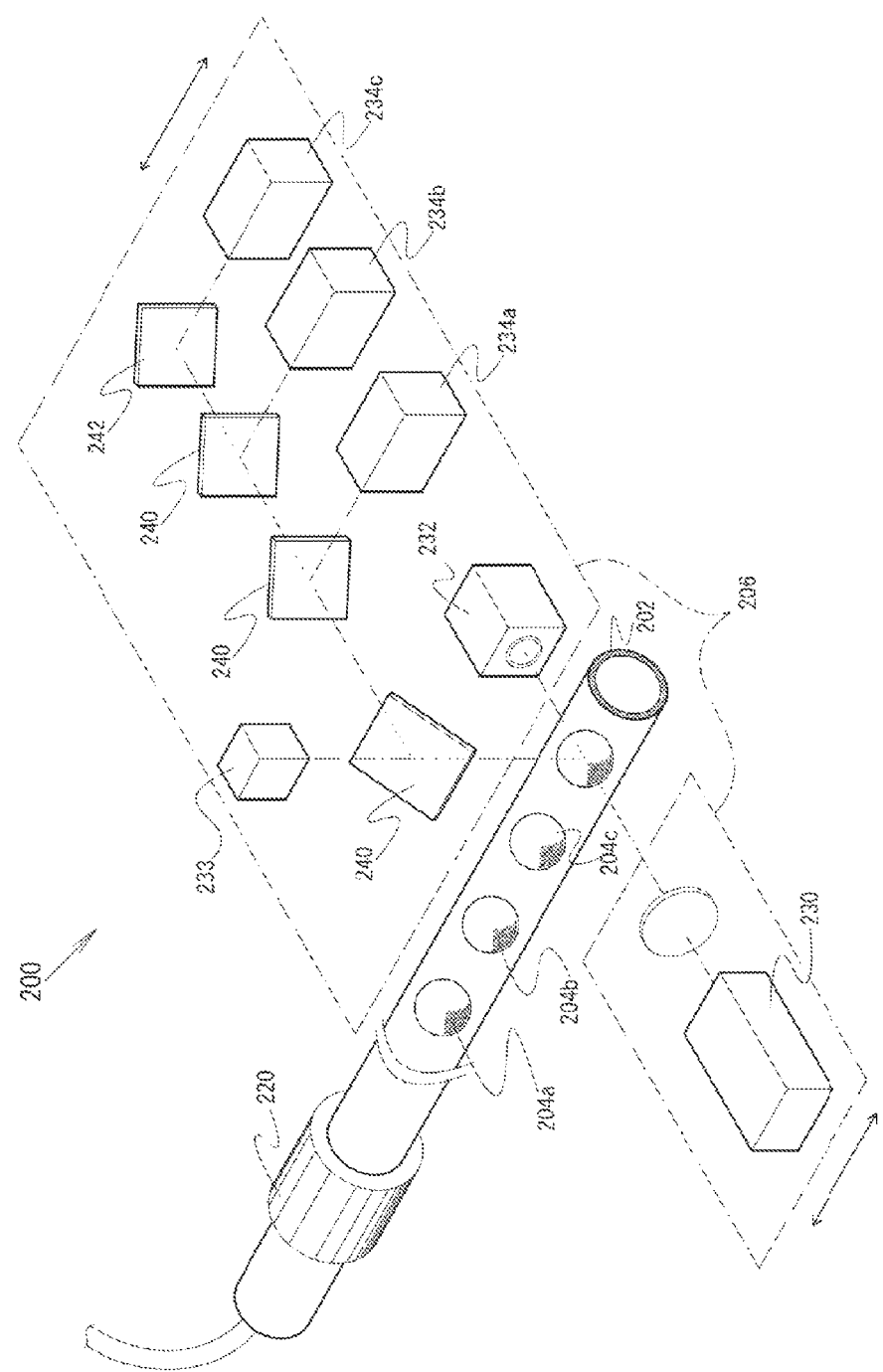
FIG. 16 schematically shows a system in which first to third microparticles are irradiated and a target bio-related substance is quantified based on the fluorescence from each microparticle.
Figure 17:
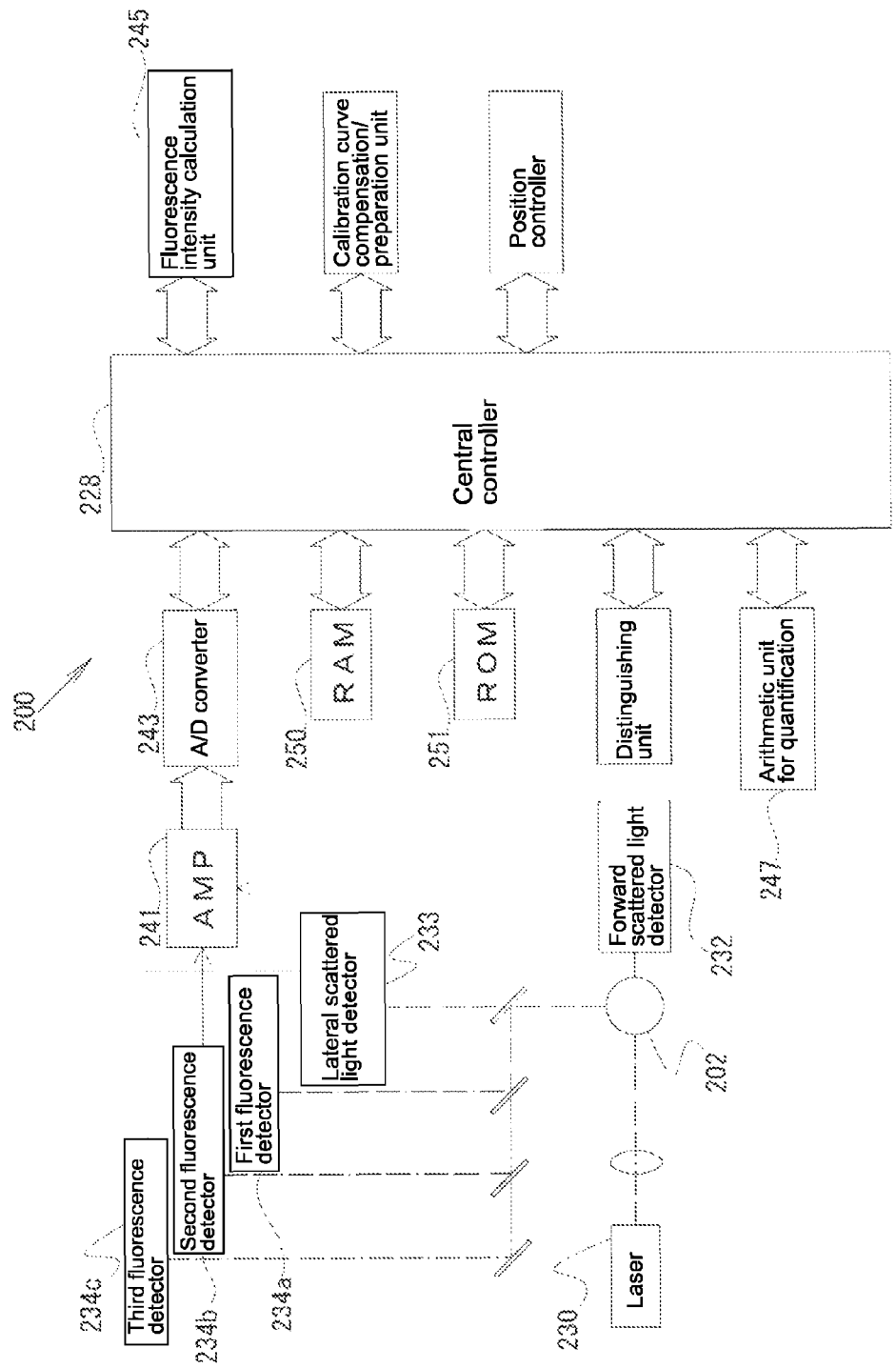
FIG. 17 is a functional block diagram of a system in which first to third microparticles are irradiated and a target bio-related substance is quantified based on the fluorescence from each microparticle.

As shown in FIGS. 16 and 17, a quantification system 200 comprises a cylindrically shaped transparent assay tube 202, first to third microparticles 204a to 204c, a detection system 206 for irradiating the first to third microparticles 204a to 204c in the assay tube 202 with excitation light to detect a target bio-related substance, an arithmetic unit (described later) for quantifying the bio-related substance based on detection signals from the detection system 206, and so on.

The first to third microparticles 204a to 204c may be composed of organic materials (e.g., latex, polyvinyl chloride, polystyrene, polypropylene, polyurethane, latex), inorganic magnetic materials (e.g., iron, Fe304, γ-Fe203, iron hydroxide, iron oxide hydrate, iron oxide, mixed iron oxide), composite materials of polymer materials with ferrite, etc.

As to the shape and size of the first to third microparticles 204a to 204c, for example, they may be formed into a spherical shape with a diameter of 0.05 mm to 10.0 mm, preferably a spherical shape with a diameter of 0.1 mm to 5.0 mm. Alternatively, each microparticle may be formed into a spherical shape with a diameter of 0.01 µm to 300 µm, preferably a spherical shape with a diameter of 0.1 µm to 50 µm.

The first to third microparticles 204a to 204c are stained or colored in a well-known manner for the purpose of distinguishing them from each other. As to preparation of the individual microparticles 204a to 204c, some techniques are known, for example, a fluorescent dye is mixed during polymerization of each microparticle, the surface of each microparticle formed is copolymerized with a fluorescent dye, or alternatively, each microparticle is stained. The spectral properties of fluorescent colorants for microparticles are required to somewhat resemble those of fluorescent dyes in fluorescent labels to be provided to microparticles.

As to colored embodiments of the microparticles, for example, the first to third microparticles 204a to 204c may be mixed with or immobilized on their surface with fluorescent colorants of a color system with varying tones (e.g., a red color system whose color saturation varies gradually), or alternatively, may be mixed with or immobilized on their surface with fluorescent colorants of a mixed color system formed by mixing a first color system with varying tones and a second color system with varying tones, which is a distinct system from the first color system.

If the total number of the first to third microparticles is large (e.g., several tens), the mixed color system shown above is used to give different levels of lightness, color phase and color saturation for each microparticle, whereby the respective microparticles can be distinguished from each other. Although the first to third microparticles 204a to 204c may be of the same or different size, the first to third microparticles may be prepared to have different particle sizes, in addition to different levels of lightness, color phase and color saturation during fluorescence emission, whereby the respective microparticles can be distinguished more reliably upon evaluating the particle size of each microparticle.

On the surface of the first microparticle 204a, a substance capable of specifically binding to a target bio-related substance is immobilized. For example, if an antigen is used as a target bio-related substance, an antibody (primary antibody) specifically binding to this antigen is immobilized on the first microparticle surface. The substance to be immobilized on the microparticle surface is not limited to this example and may be changed as appropriate. For example, when an antigen, a receptor, a DNA probe, an amino acid or the like is immobilized on the microparticle surface, an antibody, a ligand, a complementary strand DNA, an enzyme or the like can be captured.

After the target bio-related substance is captured by the first microparticle, a fluorescent label specifically binding to the target bio-related substance is allowed to bind.

For example, in a case as described above where the target bio-related substance is an antigen, after the antigen as a target bio-related substance is bound to the first microparticle, an antibody (secondary antibody) capable of specifically binding to this antigen and provided with a fluorescent dye is allowed to bind to the antigen.

Examples of a fluorescent dye for fluorescence labeling include FITC (fluorescein), PE®, PreCP®, PE-Texas Red™, PE-Cy5™, PE-Cy5.5, PE-Cy7, PreCP-Cy5.5, APC-Cy7, AMCA®, Cascade Blue®, TRITC, Cy3, Texas Red®, Cy5, Cy5.5, APC, Marina Blue®, Cascade Yellow™, rhodamine, cyanine, etc.

FIG. 16 shows an embodiment of such a fluorescence-based quantification system for a bio-related substance. As shown in FIG. 16, a quantification system 200 for a bio-related substance comprises a dispensing nozzle 220, in which the bio-related substance assay tube 202 is to be mounted. The tip of the assay tube 202 is open, and the assay tube 202 mounted in the dispensing nozzle 220 can suck up and discharge a liquid through this opening (not shown). The assay tube 202 is formed into a nearly cylindrical shape, and the first to third microparticles 204a to 204c are aligned along the longitudinal direction of the opening formed in this tube. It should be noted that the mounted posture of the assay tube 202 may be determined as appropriate. For example, the assay tube may be mounted such that the longitudinal direction of the tube extends vertically or such that the longitudinal direction of the tube extends horizontally.

The detection system 206 and the assay tube 202 are configured such that the detection system 206 can move relatively to the assay tube 202 along the longitudinal direction of the assay tube 202. Thus, the detection system 206 is allowed to move while keeping the assay tube 202 in a fixed position, or alternatively, the assay tube 202 is allowed to move while keeping the detection system 206 in a fixed position. For receiving fluorescence from any of the first to third microparticles upon irradiation with a laser, the detection system 206 is properly set in place relative to the assay tube 202.

The detection system 206 comprises an excitation light emission unit for emitting excitation light, a first light separation system for separating excitation light and fluorescence, a second light separation system for dividing fluorescence into each wavelength, a fluorescence detector for receiving the light from each light separation system, etc. Specific examples of such a detector include, for example, a detector equipped with a confocal optical system which allows measurement of a microscopic object, and such a detector equipped with a confocal optical system comprises, for example, a laser light source 230 for emitting excitation light of different wavelengths as an excitation light emission unit, as well as a photodiode and a photomultiplier (hereinafter referred to as PMT) or the like as a fluorescence detector. The light source for emitting excitation light outputs the intensity and wavelength sufficient to excite a fluorescent dye, and possible light sources having such functions include not only a laser, but also other light sources such as a mercury lamp, a xenon lamp, an LED, etc. Likewise, light receiving elements are not limited to the above photodiode 232 and PMT 234, and other sensors or the like may be used as appropriate.

To cause fluorescence emission from the microparticles 204a to 204c aligned in the assay tube 202, the detection system 206 is first set in place relative to the microparticles 204a to 204c to be measured, and the microparticles 204a to 204c are then irradiated with excitation light. Upon receiving the excitation light, the microparticles 204a to 204c each emit forward scattered light, lateral scattered light and fluorescence. The forward scattered light is detected by a forward scattered light detector 232, the lateral scattered light is detected by a lateral scattered light detector 233, and the fluorescence is detected by first to third fluorescence detectors 234. The forward scattered light detector 232 may be, for example, a photodiode, while the lateral scattered light detector 233 and the first to third fluorescence detectors 234a to 234c may each be, for example, a PMT. In these photodiode and PMT, analog electrical signals are formed by photoelectric conversion.

The wavelength of the excitation light emitted from the laser 230 may vary (e.g., 488 nm, 532 nm or 633 nm), and the light source to be used may be selected as appropriate for the properties of fluorescent dyes used for fluorescent labeling of the first to third microparticles 204a to 204c. In particular, to ensure the use of multiple fluorescent dyes, the system may be equipped with a light source capable of outputting laser light of different wavelengths.

In a case where a mixed color system is used as a fluorescent colorant for the first to third microparticles, fluorescence is received by the first to third fluorescence detectors 234a to 234c corresponding to the respective fluorescent colors of the fluorescent dyes. Alternatively, in a case where a single color system whose color saturation varies gradually is used as a fluorescent colorant for the first to third microparticles 204a to 204c, fluorescence is received by a corresponding single fluorescence detector 234a.

In a case as described above where multiple fluorescent dyes are used, fluorescence is divided into component light beams by the light separation system, and these component light beams are introduced into the fluorescence detectors 234a to 234c provided respectively for the component light beams. The light separation system 235 comprises a dichroic mirror 240 and a lens, pinhole or mirror 242, whose relative position is determined such that the detection system 206 is optimally positioned relative to the assay tube 202. It should be noted that although the dichroic mirror 240 is illustrated as an optical member for light separation in the above embodiment, the optical member for light separation is not limited thereto and may be replaced as appropriate with a more inexpensive polarization beam splitter, etc.

The lateral scattered light detector 233 and the first to third fluorescence detectors 234a to 234c send analog light receiving signals based on voltage levels corresponding to the received light intensity to an amplifier 241, which is described later. The light receiving signals from the lateral scattered light detector 233 and the first to third fluorescence detectors 234a to 234c are amplified by the amplifier 241 and then converted into digital signals by an A/D converter 243 to form fluorescence intensity data. The fluorescence intensity data thus formed is sent to a fluorescence intensity calculation unit 245.

The fluorescence intensity calculation unit 245 calculates the fluorescence intensity of the first to third microparticles 204a to 204c on the basis of each fluorescence intensity data from the A/D converter 243.

A distinguishing unit 253 distinguishes the first to third microparticles 204a to 204c on the basis of detection signals from the forward scattered light detection unit 232.

An arithmetic unit for quantification 247 quantifies a target bio-related substance by checking fluorescence intensity against a calibration curve.

If a calibration curve previously stored in an RAM 250 is used to quantify a bio-related substance, the fluorescence intensity of the first microparticle is corrected based on the fluorescence intensity of the second and third microparticles 204b and 204c.

If a calibration curve is prepared and used to quantify a bio-related substance, the fluorescence intensity of a plurality of second microparticles 204b on which gradually different amounts of the bio-related substance have been immobilized is used and a calibration curve is prepared during quantification of the target bio-related substance on the basis of the fluorescence intensity of these second and third microparticles 204b and 204c.

After the calibration curve is prepared, the fluorescence intensity of the first microparticle 204a calculated in the fluorescence intensity calculation unit 245 is checked against the calibration curve in the arithmetic unit for quantification 247 to thereby quantify the concentration of the target bio-related substance.

It should be noted that to avoid any influence on antigen quantification due to overlapping of fluorescence spectra between the microparticles 204a to 204c and the fluorescent dye in the secondary antibody, the arithmetic unit for quantification 247 conducts compensation (fluorescence compensation) to correct the interaction-induced effects in each fluorescence spectrum, thereby calculating the amount of the antigen.

Next, the effect of the present invention will be described. It should be noted that although an embodiment intended for antigen quantification is given below as an example, the target bio-related substance to be quantified is not limited to an antigen and it is fully possible to quantify other bio-related substances such as an antibody, a receptor, a nucleic acid, etc. Moreover, in the following embodiment, two antigens (i.e., first and second antigens) are shown as multiple bio-related substances to be quantified, but the number of target bio-related substances is not limited to two and may be either one or three or more.

The tip of the assay tube 202 mounted in the dispensing nozzle 220 is soaked in a container containing an analyte to suck up the analyte into the assay tube 202. As first microparticles 204a, the assay tube 202 comprises, for example, a microparticle on the surface of which a primary antibody capable of binding to the first antigen is immobilized, as well as a microparticle on the surface of which a primary antibody capable of binding to the second antigen is immobilized.

After a period sufficient for the antigens to bind to the primary antibodies, a labeling solution containing secondary antibodies for fluorescent labeling is sucked up into the assay tube 202. Fluorescent dyes in the secondary antibodies capable of binding to the first and second antigens differ in their fluorescent color and excitation wavelength, whereby these antigens can be distinguished and quantified separately.

After a sandwich conjugate is formed from the microparticle on which the primary antibody is immobilized, the antigen and the secondary antibody for fluorescent labeling, the detection system 206 is set in place relative to the assay tube 202 and the first to third microparticles 204a to 204c are sequentially irradiated with excitation light.

Upon receiving forward scattered light from the first to third microparticles 204a to 204c, the forward scattered light detector 232 sends detection signals to the distinguishing unit 253 where the microparticles 204a to 204c are distinguished from each other based on the detection signals from the forward scattered light detector 232.

Upon receiving fluorescence from the first to third microparticles 204a to 204c, the fluorescence detectors 234a to 234c send light receiving signals depending on the received fluorescence to the amplifier 241, and data of the received light intensity formed by A/D conversion or the like is inputted to the fluorescence intensity calculation unit 245.

The fluorescence intensity calculation unit 245 calculates the fluorescence intensity based on the fluorescence intensity data of the fluorescent dye in each secondary antibody bound to each first microparticle 204a.

If a previously prepared calibration curve is stored in the RAM 250, the fluorescence intensity of each first microparticle 204a is corrected based on the fluorescence intensity of the second and third microparticles 204b and 204c to thereby quantify each bio-related substance.

If a calibration curve is prepared during quantification of each target bio-related substance by using the fluorescence intensity of a plurality of second microparticles 204b on which gradually different amounts of each bio-related substance have been immobilized, a calibration curve is prepared based on the fluorescence intensity of the second and third microparticles 204b and 204c, and the fluorescence intensity of each first microparticle 204a is checked against the calibration curve thus prepared to quantify each target bio-related substance.

In view of the foregoing, in the quantification system 200 of the present invention, the bio-related substance assay tube 202 has the first microparticle 204a capable of binding to each target bio-related substance together with the second microparticle 204b on which a given amount of each target substance has been immobilized and the third microparticle 204c for use as a negative control, whereby correction or preparation of a calibration curve for multiple bio-related substances and quantification of these bio-related substances can be performed at a time, which enables the provision of a highly convenient quantification system for multiple bio-related substances with high quantification accuracy.

Moreover, as compared to functionally equivalent flow cytometry (cytometric bead assay), the system can be expected to have a simpler configuration because there is no need to form a stable, non-turbulent laminar flow for moving individual particles.

Further, since the bio-related substance assay tube 202 is removably mounted in the dispensing nozzle 220, the assay tube 202 can be replaced with a new one for every analyte. This eliminates the need for maintenance of a sheath flow channel and a fluid delivery system, which are required to convey microparticles, and enables the provision of a more convenient quantification system.

Furthermore, since correction or preparation of a calibration curve and quantification of multiple bio-related substances can be performed together at the same time, not only experimental accuracy, but also convenience can be improved.

In the above second embodiment, the first to third microparticles 204a to 204c are irradiated with light and their forward scattered light and lateral scattered light are detected to quantify the target bio-related substance, but the procedures used for quantification are not limited thereto and other procedures may be used as appropriate. In this bio-related substance quantification using a fluorescent label, it is sufficient to observe a fluorescence event from the fluorescent label bound to the bio-related substance, and appropriate modifications may be made to the optical system which allows observation of a fluorescence event, the light receiving unit which receives subject light from the optical system, and the arithmetic unit including an electronic circuit which calculates fluorescence intensity based on electrical signals from the light receiving unit. For example, although the optical system by means of forward/lateral scattered light is illustrated in the above embodiment, it is also possible to use an optical system mainly by means of reflected light. Moreover, as a light receiving unit, a high-sensitivity CCD sensor may be used instead of a PMT, and the configuration of this system can be modified as appropriate for detailed design purposes.

In the above fluorescence measurement, the assay tube 202 in which the first to third microparticles 204a to 204c have been held is shown as an example, although fluorescence from the first to third microparticles may be measured using a capillary-type assay tube having an inner cavity into which the individual microparticles are to be sucked up in a line.

Examples of such an assay tube include those having a long and narrow inner cavity with an orifice size of several microns to several tens of microns, through which microparticles with a particle size of several microns to several tens of microns can pass one at a time. Examples of materials used to form such assay tubes include glass materials (e.g., quartz glass), polymer materials (e.g., plastics), etc.

The first to third microparticles are sucked up through the tip of the assay tube mounted in the nozzle into the inner cavity of the assay tube, where the microparticles are aligned and held in a line, and these aligned first to third microparticles are irradiated with excitation light and measured for their fluorescence.

In such an embodiment, t he measurement system also achieves the same functions as in the case of using the assay tube in which first to third microparticles have been held, so that the system allows quantification of a target bio-related substance.

It should be noted that although the first to third microparticles are irradiated with excitation light in a state held in the inner cavity of the assay tube in the above embodiment, the first to third microparticles may be irradiated with excitation light while sucking up them or while discharging the sucked microparticles in order to reduce variations in fluorescence intensity data. By measuring the fluorescence intensity of each microparticle in such an embodiment, it can be expected to reduce variations in their fluorescence intensity data.

EXAMPLES

The following shows examples of the procedures illustrated in the first embodiment for chemiluminescence-based quantification of a single bio-related substance.

Example 1

Based on the quantification system 30 shown above, the following procedures were performed:

(a) the step of introducing an analyte into a light-transmissible assay tube whose inner cavity is charged with a first microparticle on which a substance capable of binding to a target bio-related substance to be measured is immobilized, a second microparticle on which the above bio-related substance is immobilized in a given amount, and a third microparticle for use as a negative control;

(b) the step of introducing a labeling solution into the assay tube receiving the analyte to provide a label to each microparticle;

(c) the step of introducing a substrate solution, which allows light emission from each label, into the assay tube to cause light emission from the first to third microparticles; and (d) the step of quantifying the bio-related substance based on the emission intensity of the first to third microparticles.

According to these steps, for example, egg white lysozyme (antigen) was quantified. Details are shown below.

In the case of quantifying egg white lysozyme (HEL) as a bio-related substance, for example, anti-egg white lysozyme monoclonal antibody 1 (hereinafter referred to as HELmAB1) was used as an antibody against the antigen to be measured, while anti-egg white lysozyme monoclonal antibody 2 (anti-HELmAB2) was used as an enzyme label.

To quantify egg white lysozyme using the quantification system 30 shown above, first to third microparticles 14 to 16 (see FIG. 5) to be held in the inner cavity of the assay tube 13 were prepared.

Preparation of the first to third microparticles 14 to 16 was accomplished as follows. It should be noted that the following description is provided as an example and is not intended to limit the present invention.

1. Preparation of First to Third Microparticles
(1) Washing of Beads

Roughly polished nitride beads required for quantification were transferred to a test tube of 1.5 ml volume, washed with acetone, and then washed three times with 1 ml of phosphate buffer containing 0.05% sodium azide.

(2) Immobilization of Beads

Assay bead for egg white lysozyme (first microparticle): To a test tube containing the starting beads, 1 ml of anti-HEL C1mAB solution diluted to 10 µg/ml with phosphate buffer containing 0.05% sodium azide was added and allowed to stand overnight at 4° C. (immobilization). If necessary, the test tube containing the beads and the sodium azide-containing phosphate buffer was shaken in a vortex mixer.

Internal standard bead 1 (second microparticle for emission intensity compensation): To a test tube containing the starting beads, a purified HEL protein (antigen) solution adjusted to 0.6 ng/ml with phosphate buffer containing 0.05% sodium azide was added and allowed to stand overnight at 4° C. (immobilization). If necessary, the test tube containing the beads and the sodium azide-containing phosphate buffer was shaken in a vortex mixer.

Internal standard bead 2 (second microparticle for emission intensity compensation): To a test tube containing the starting beads, a purified HEL protein (antigen) solution adjusted to 10.0 ng/ml with phosphate buffer containing 0.05% sodium azide was added and allowed to stand overnight at 4° C. (immobilization). If necessary, the test tube containing the beads and the sodium azide-containing phosphate buffer was shaken in a vortex mixer.

Analyte blank bead (third microparticle for use as a negative control): To a test tube containing the starting beads, 1 ml of phosphate buffer containing 0.05% sodium azide was added and allowed to stand overnight at 4° C. (immobilization). If necessary, the test tube containing the beads and the sodium azide-containing phosphate buffer was shaken in a vortex mixer.

(3) These three types of immobilized beads were washed several times with phosphate buffer containing 0.05% sodium azide, and then blocked with 200 µl of phosphate buffer containing 1% BSA (bovine serum albumin) by being allowed to stand at room temperature.

Next, the beads thus prepared were each introduced into an assay tube and held in the inner cavity of the assay tube. In this case, light-shielding beads were interposed between the individual beads.

The above three types of beads were washed twice with a washing solution (buffer containing 0.05% Tween 20), and then introduced into the assay tube and fixed in its inner cavity in the following order: the internal standard beads, the light-shielding bead, the assay bead for egg white lysozyme, the light-shielding bead, the analyte blank bead, and the light-shielding bead.

The assay tube thus prepared was mounted in the nozzle equipped in the quantification system. After mounting the assay tube in the nozzle, an analyte was introduced into the assay tube as follows. This was accomplished, for example, according to an automation program of the quantification system.

Into the assay tube receiving the analyte, a labeling solution was introduced. For example, according to an automation program of the quantification system, the tube was reacted for 1 hour with biotinylated anti-HEL C2mAB diluted to 1 µg/ml, washed with a washing solution, and then reacted for 30 minutes with streptavidin-HRP diluted 5000-fold.

After introducing the labeling solution into the assay tube, a chemiluminescent substrate (e.g., Super Signal West Femto Maximum Sensitivity Substrate (Thermo scientific)) was introduced into the assay tube to cause chemiluminescence from each bead, followed by measuring the emission intensity of each bead to quantify the target egg white lysozyme.

It should be noted that although two types of second microparticles were prepared in this example, a single type of second microparticle or three or more types of second microparticles may be prepared.

Example 2

Based on the quantification system 175 shown above, the following procedures were performed:

(a) the step of introducing an analyte into a light-transmissible assay tube whose inner cavity is charged with a first microparticle on which a substance capable of binding to a target bio-related substance to be measured is immobilized, a plurality of second microparticles on which different amounts of the above bio-related substance are immobilized, and a third microparticle for use as a negative control;

(b) the step of introducing a labeling solution into the assay tube receiving the analyte to provide a label to each microparticle;

(c) the step of introducing a substrate solution, which allows light emission from each label, into the assay tube to cause light emission from the first to third microparticles; and (d) the step of quantifying the bio-related substance based on the emission intensity of the first to third microparticles.

It should be noted that the first to third microparticles may be aligned either in a single tube or in separate tubes. To improve quantification accuracy, it is desired that the first to third microparticles are measured for light emission either simultaneously or continuously.

According to these steps, for example, egg white lysozyme (antigen) was quantified. Details are shown below.

In the case of quantifying egg white lysozyme (hereinafter referred to as HEL) as an antigen to be measured, anti-egg white lysozyme monoclonal antibody 1 (hereinafter referred to as HELmAB1) was used as an antibody against the antigen to be measured, while anti-HELmAB2 was used as an enzyme label. It should be noted that the detailed description given here is merely an example and is not intended to limit the contents of the present invention.

First, second microparticles required to prepare a calibration curve used during quantification of egg white lysozyme were prepared as follows.

(1) For example, 50 roughly polished nitride beads were introduced into a test tube of 1.5 ml volume, washed with acetone, and then washed three times with 1 ml of phosphate buffer containing 0.05% sodium azide.

(2) Then, a plurality of purified HEL protein (antigen) solutions prepared to have different concentrations by serial two-fold dilution (starting from 20 ng/ml) with phosphate buffer containing 0.05% sodium azide were dispensed in 100 μl volumes into small test tubes, and each test tube containing sodium azide-containing phosphate buffer at each concentration was supplemented with the acetone-washed roughly polished nitride beads in an appropriate amount and allowed to stand overnight while being kept at 4° C. (immobilization). If necessary, the test tubes containing the beads and the sodium azide-containing phosphate buffer were each shaken in a vortex mixer.

(3) After being allowed to stand overnight, the beads were washed with phosphate buffer containing 0.05% sodium azide and further blocked with 200 μl of phosphate buffer containing 1% BSA (bovine serum albumin).

(4) After washing twice with a washing solution (phosphate buffer containing 0.05% Tween 20), the beads were introduced into an assay tube. It should be noted that light-shielding beads were interposed between the individual beads.

Next, a first microparticle for capturing a target bio-related substance, a second microparticle for use as a positive control, and a third microparticle for use as a negative control were prepared.

(1) Washing of Beads

Roughly polished nitride beads required for quantification were transferred to a test tube of 1.5 ml volume, washed with acetone, and then washed several times with 1 ml of phosphate buffer containing 0.05% sodium azide.

(2) Immobilization of Beads

Assay bead for egg white lysozyme (first microparticle): To a test tube containing the starting beads, a purified HEL protein (antigen) solution adjusted to 2.5 ng/ml with phosphate buffer containing 0.05% sodium azide was added and allowed to stand overnight while being kept at 4° C. (immobilization). If necessary, the test tube containing the beads and the sodium azide-containing phosphate buffer was shaken in a vortex mixer.

Positive control bead (second microparticle): To a test tube containing the starting beads, a purified HEL protein (antigen) solution adjusted to 2.5 ng/ml with phosphate buffer containing 0.05% sodium azide was added and allowed to stand overnight at 4° C. (immobilization). If necessary, the test tube containing the beads and the sodium azide-containing phosphate buffer was shaken in a vortex mixer.

Negative control blank bead (third microparticle): To a test tube containing the starting beads, 1 ml of phosphate buffer containing 0.05% sodium azide was added and allowed to stand overnight at 4° C. (immobilization). If necessary, the test tube containing the beads and the sodium azide-containing phosphate buffer was shaken in a vortex mixer.

(3) Each bead was washed twice with phosphate buffer containing 0.05% sodium azide, and then blocked with 200 μl of phosphate buffer containing 1% BSA (bovine serum albumin) by being allowed to stand at room temperature.

The thus prepared assay bead for egg white lysozyme, positive control bead and blank bead were introduced into the assay tube where the beads for calibration curve preparation had been held. In this case, light-shielding beads were interposed as appropriate between the individual beads. For example, the above beads were washed, e.g., twice with a washing solution (phosphate buffer containing 0.05% Tween 20), and then introduced into the assay tube in the following order: the positive control bead, the light-shielding bead, the assay bead for egg white lysozyme, the light-shielding bead, the blank bead, and the light-shielding bead. This assay tube was mounted in the nozzle in the quantification system.

After mounting the assay tube in the quantification system, an analyte was introduced into the assay tube. This was accomplished, for example, according to an automation program of the quantification system by filling the assay tube with a diluted or undiluted analyte solution.

Into the assay tube receiving the analyte, a labeling solution was introduced. For example, according to an automation program of the quantification system, the tube was reacted for 1 hour with biotinylated anti-HEL C2mAB diluted to 1 μg/ml with a washing solution, washed with the washing solution, and then reacted for 30 minutes with streptavidin-HRP (horse radish peroxidase) diluted 5000-fold.

Into the assay tube receiving the labeling solution, a chemiluminescent substrate solution (e.g., Super Signal West Femto Maximum Sensitivity Substrate (Thermo scientific)) was introduced to cause chemiluminescence from each bead, followed by measuring the emission intensity of each bead.

Example 3

This example illustrates an assay tube and a quantification system, which are designed to quantify multiple bio-related substances based on chemiluminescence from first to third microparticles.

As an approach to quantify multiple bio-related substances, two measurement systems, i.e., first and second measurement systems were used here, and antigens were selected as target bio-related substances.

[Overview]

As shown in FIG. 15(*a*), an assay tube for use in the first measurement system comprises reference beads (reference microparticles) represented by bead Nos. 1, 3, 5 and 7, as well as a plurality of first beads (bead Nos. 11, 13, 15 and 17) for measuring unknown bio-related substances.

Further, as shown in FIG. 15(*b*), an assay tube for use in the second measurement system comprises reference beads (reference microparticles) represented by bead Nos. 1, 3, 5 and 7, as well as second beads for use as a positive control (bead Nos. 11, 13, 15 and 17) which are prepared for four bio-related substances to be quantified in the first measurement system.

[First Measurement System]

1. Preparation of First Beads (First Microparticles)

In a case where the target bio-related substances were, for example, a plurality of antigens, a plurality of antibodies specifically reacting the respective antigens were immobilized on separate silicon nitride beads.

2. Preparation of Second Beads (Second Microparticles)
(1) Washing of Beads

For example, silicon nitride beads (e.g., Tsubaki Nakashima Co., Ltd., Japan) serving as a base for second beads were washed. This washing was accomplished, for example, by ultrasonication in PBS for 10 minutes.
(2) Immobilization of Beads A protein was immobilized on the washed silicon nitride beads. As a protein, for example, 4-hydroxy-3-nitrophenylacetyl (hereinafter referred to as NP) serving as a hapten was conjugated with human serum albumin (hereinafter referred to as HSA) and used for this purpose. This NP-HSA conjugate was immobilized on the silicon nitride beads.

NP-HSA solutions may be prepared to have gradually different concentrations. For example, solutions prepared at seven concentrations (10, 5, 2.5, 1.2, 0.6, 0.3 and 0.1 µg/ml) were used.

It should be noted that as a third bead for use as a negative control (third microparticle), any bead may be used as long as it is inert to the target bio-related substances. F or example, a blank bead treated to prevent binding of the target bio-related substances was used.

3. Filling of First to Third Beads into Assay Tube

The first to third beads were aligned via silicon carbide beads for light-shielding purposes.

For example, these beads were aligned in the inner cavity of an assay tube in the following order: the second bead prepared by being soaked in the NP-HSA solution of 10 µg/ml concentration, the second bead prepared similarly by being soaked in the 5 µg/ml solution, the second bead prepared similarly by being soaked in the 2.5 µg/ml solution, the second bead prepared similarly by being soaked in the 1.2 µg/ml solution, the second bead prepared similarly by being soaked in the 0.6 µg/ml solution, the second bead prepared similarly by being soaked in the 0.3 µg/ml solution, the second bead prepared similarly by being soaked in the 0.1 µg/ml solution, the blank bead, and the first bead. Light-shielding beads were interposed and fixed between the individual beads.

4. First Measurement

Calibration curves used for quantification of multiple bio-related substances and for quantification of each bio-related substance were prepared and stored in a memory in the quantification system.

After the assay tube holding the individual beads was mounted in a nozzle in the quantification system, an analyte, a labeled antibody and a substrate solution were introduced into the assay tube as follows. The tube was first reacted with an analyte of unknown concentration and then with a labeling solution (a mixture of biotin-labeled anti-NP antibody and biotin-labeled anti-analyte antibody), finally followed by suction of a substrate solution into the assay tube to cause light emission. Chemiluminescence from each bead was detected by a detector through a transmission optical system (e.g., an optical fiber) to calculate the emission intensity of each bead on the basis of output signals from the detector.

[Second Measurement System]

After completion of the first measurement, an assay tube holding a plurality of second beads on which known amounts of the above antigens were immobilized was mounted in the quantification system to measure the emission intensity of each bead.

For this purpose, the assay tube used in the above first measurement system was subjected to a certain treatment and then used. In order to use again the assay tube used in the first measurement system, an acidic solution was sucked up into the assay tube and contacted with each bead to remove the antigens, the labeled antibodies and others captured on the beads during the first measurement. After regeneration of the assay tube, the bio-related substances of known concentrations (purified antigen controls) were allowed to be captured by beads designed to quantify the respective bio-related substances, and then used for second measurement to confirm that the beads functioned normally and quantitatively. The plurality of silicon nitride beads used for measurement of the bio-related substances in the analyte were allowed to serve as a positive control by being regenerated and reacted with the antigens of known concentrations. In this way, the assay tube used in the first measurement system was subjected to a certain treatment and used again in the second measurement system.

Along with confirming the correlation between the first measurement system and the second measurement system on the basis of the emission intensity of the reference beads, it was determined that the measurement systems were proper, based on differences in emission intensity between the second beads for use as a positive control and the third bead for use as a negative control.

The emission intensity of each bio-related substance detected in the first and second measurement systems was checked against the calibration curve for each substance read from the memory to quantify each bio-related substance. In the manner as described above, multiple bio-related substances were quantified.

Example 4

[Overview]

On silicon nitride beads, 4-hydroxy-3-nitrophenylacetyl (NP)-human serum albumin (HSA) was immobilized at varying concentrations, and the resulting beads were used as compensation beads. The target substance capture beads used were silicon nitride beads on which anti-ovalbumin (OVA) antibody was immobilized to allow detection of OVA as an antigen.

[Major Materials Used in Experiment]
Silicon nitride beads (Tsubaki Nakashima Co., Ltd., Japan), which were used to prepare compensation beads and OVA detection beads
Silicon carbide beads (Tsubaki Nakashima Co., Ltd., Japan), which were used as light-shielding beads
NP-HSA
OVA
Biotin-labeled anti-NP antibody
Biotin-labeled anti-OVA antibody (for detection) and anti-OVA antibody (for immobilization on beads)
Avidin-HRP
Lumi-Light (a substrate for light emission, available from Roche)

[Preparation of Second Beads]
(1) Washing of silicon nitride beads: The beads were washed by ultrasonication in PBS (buffer) for 10 minutes.
(2) Immobilization of protein (NP-HSA): NP6-HAS was prepared in 200 µl volumes at concentrations of 10, 5, 2.5, 1.2, 0.6, 0.3 and 0.1 µg/ml.
(3) Into tubes, NP-HAS (200 µl) was introduced and the washed beads were added in groups of 10, followed by shaking overnight to immobilize the protein.
(4) After washing twice with PBS, the beads were blocked with 1% BSA-containing PBS while shaking for 2 hours.

[Preparation of First Beads for OVA Capture]

(1) To 200 µl of an anti-OVA antibody solution prepared at a concentration of 1.64 mg/ml, the washed beads were added in groups of 10 and shaken overnight to immobilize the antibody.

(2) After washing twice with PBS, the beads were blocked with 1% BSA-containing PBS while shaking for 1 hour.

After the buffer was removed, a 1 pg/ml OVA solution (200 µl) was added and reacted.

[Filling into Assay Tube]

One first bead for OVA capture serving as a first microparticle and seven second beads were aligned via silicon carbide beads for light-shielding purposes.

Figure 18:
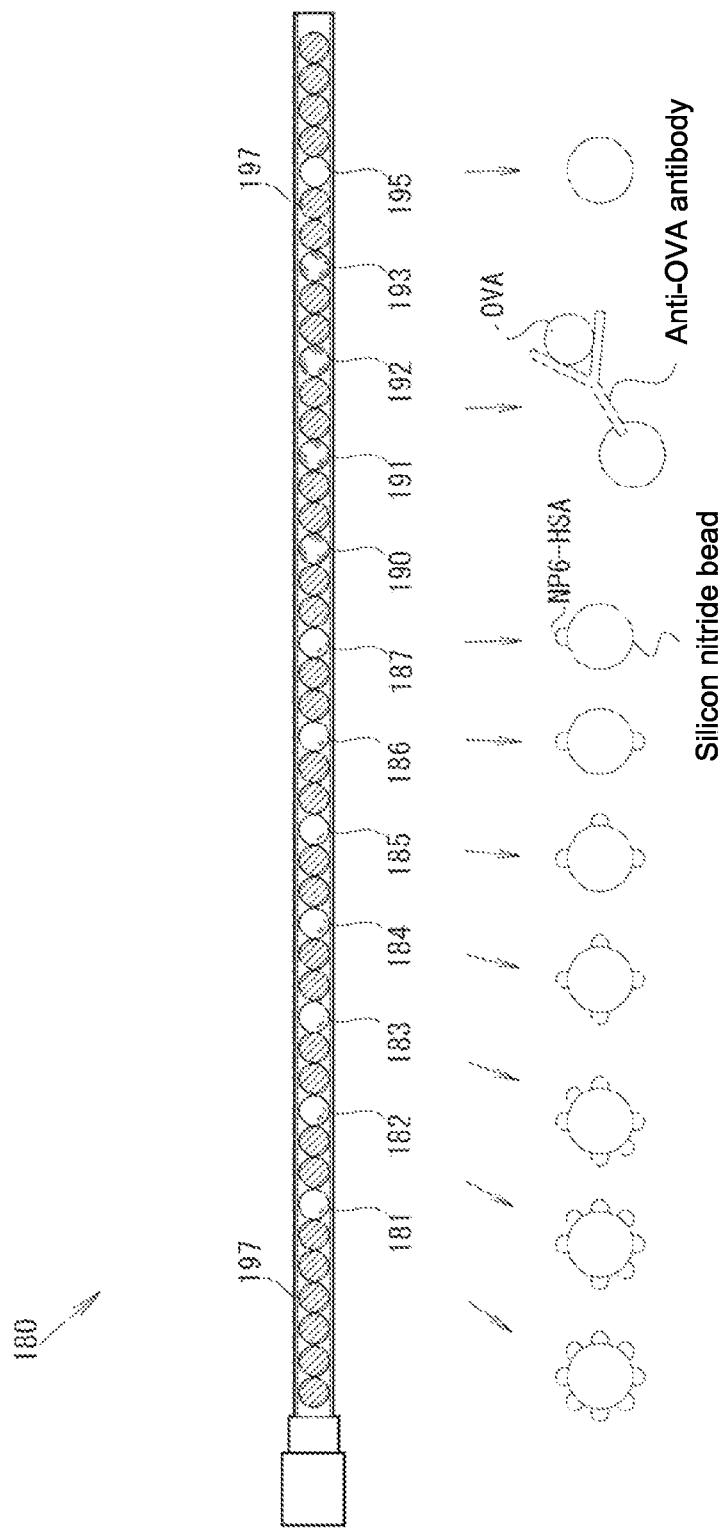
FIG. 18 schematically shows a tube in which beads carrying NP-HSA immobilized thereon and a bead carrying anti-OVA antibody immobilized thereon are aligned via light-shielding beads.

As shown in FIG. 18, the inner cavity of an assay tube 180 was charged with the second bead 181 prepared by being soaked in the NP-HSA solution of 10 µg/ml concentration, the second bead 182 prepared similarly by being soaked in the 5 µg/ml solution, the second bead 183 prepared similarly by being soaked in the 2.5 µg/ml solution, the second bead 184 prepared similarly by being soaked in the 1.2 µg/ml solution, the second bead 185 prepared similarly by being soaked in the 0.6 µg/ml solution, the second bead 186 prepared similarly by being soaked in the 0.3 µg/ml solution, the second bead 187 prepared similarly by being soaked in the 0.1 µg/ml solution, the first bead 190 for OVA capture, and the blank bead 195 in this order. These particles were each charged via two light-shielding beads 197.

[Reaction Using Automatic System]

Biotin-labeled anti-NP antibody (5 µg/ml) and biotin-labeled anti-OVA antibody (0.5 µg/ml) were each prepared in a volume of 100 µl and introduced into a reagent cartridge, which was then mounted in a chromatography apparatus (Purelumn®, GE HealthCare) to automatically perform the steps of tube washing, reaction with the biotinylated antibodies and reaction with StreptAvidin-HRP.

[Measurement with Dedicated Detector]

A substrate for light emission (Lumi-Light) was sucked up into the tube after automatic reaction, followed by measurement with a dedicated detector (BISTnner®, Precision System Science Co., Ltd., Japan).

[Results of Measurement]

Figure 19:
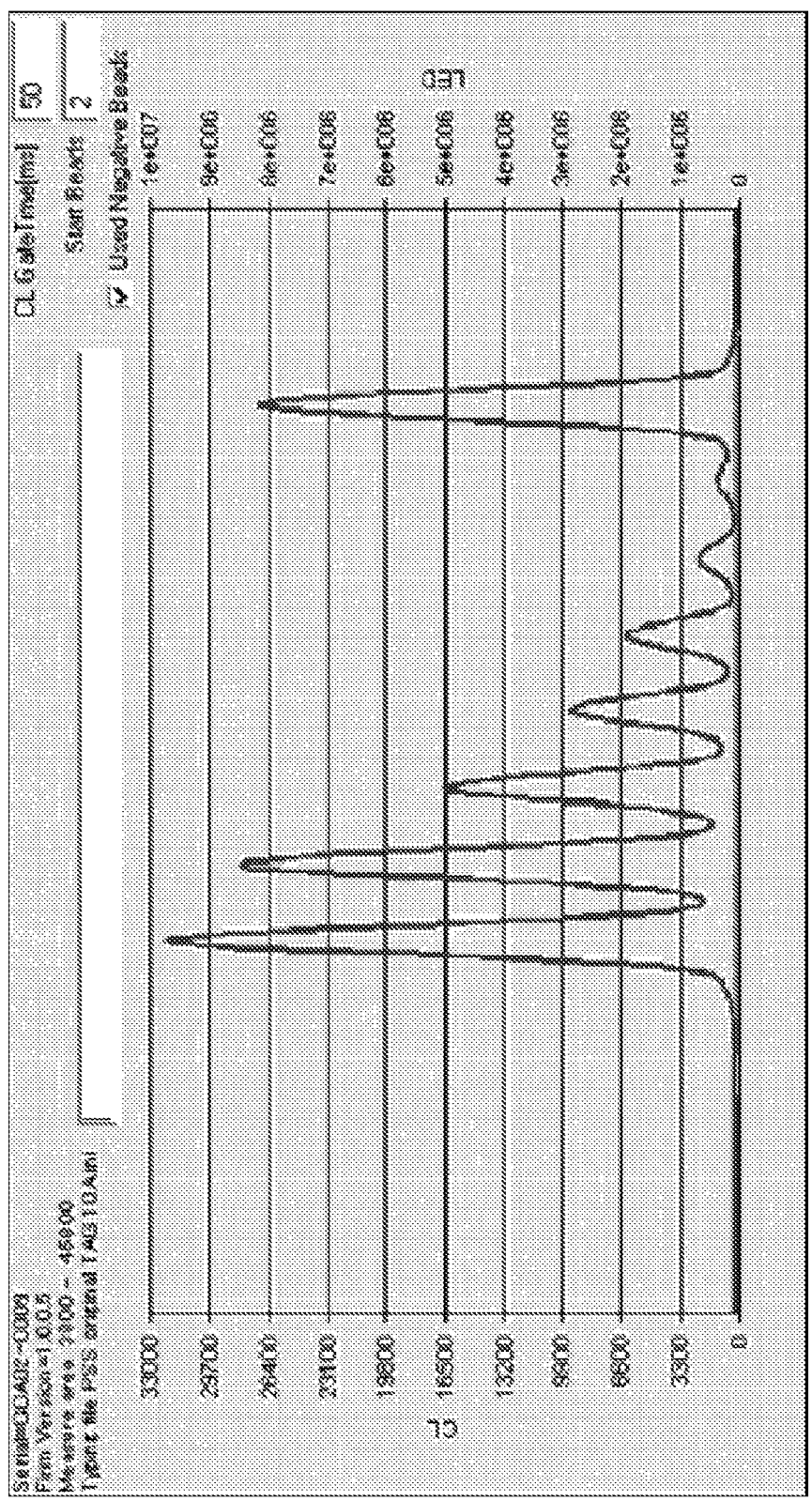
FIG. 19 is a graph showing the emission intensity of a label on OVA obtained by using a tube comprising a bead carrying anti-OVA antibody immobilized thereon.

As shown in FIG. 19, light emission signals were obtained for the NP-HAS-immobilized beads having NP-HAS concentrations of 10 µg/ml, 5 µg/ml, 2.5 µg/ml, 1.2 µg/ml, 0.6 µg/ml, 0.3 µg/ml and 0.1 µg/ml, and for the first bead (listed from the left).

[Conclusion]

Figure 20:
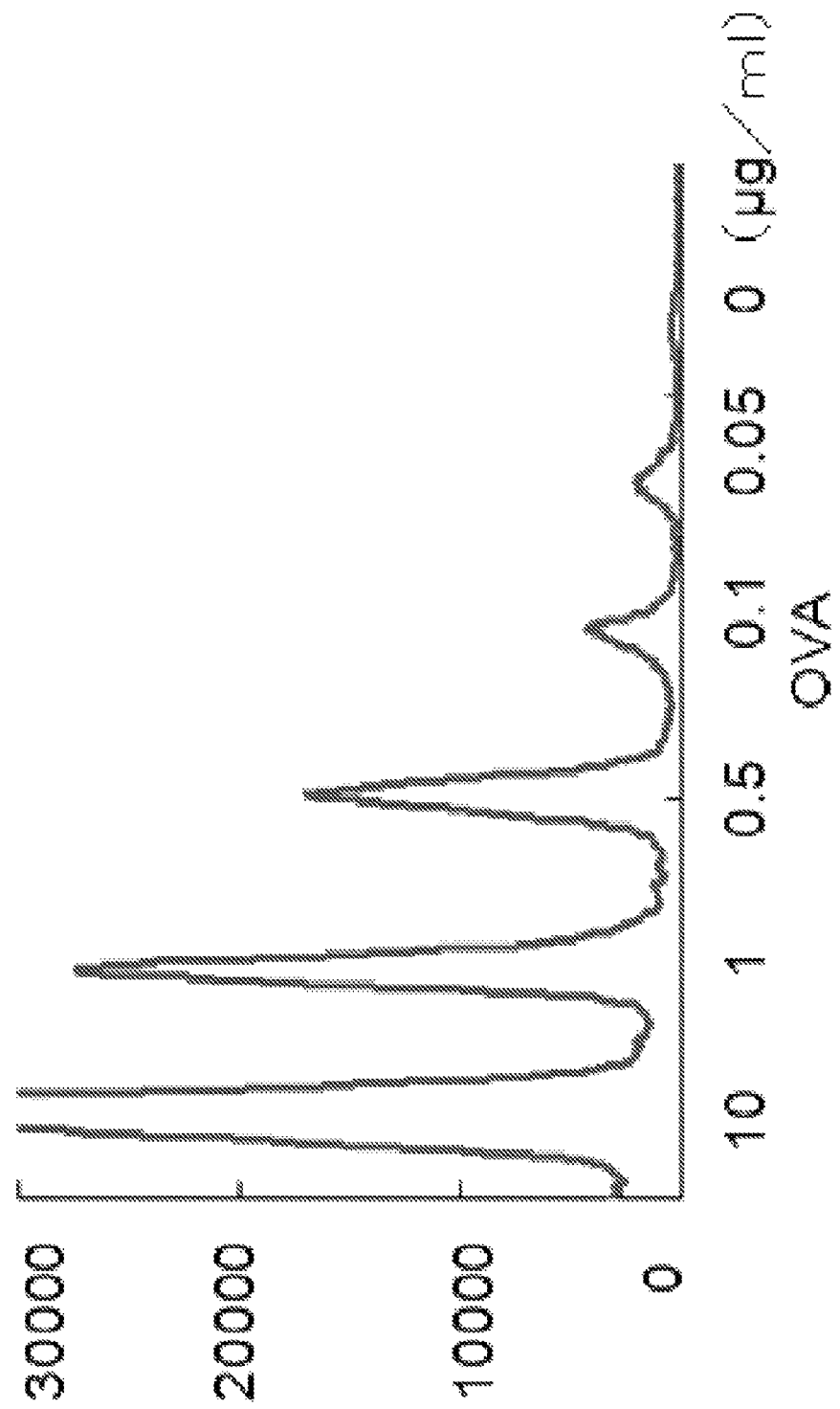
FIG. 20 is a graph of a calibration curve for OVA quantification based on the emission intensity of OVA.

Based on a previously obtained graph for OVA quantification (see FIG. 20), it can be determined that the fluorescence intensity of the first bead for OVA capture corresponds to light emission signals at an OVA concentration of 1 µg/ml.

EXPLANATION OF REFERENCE NUMERALS

2: Bio-related substance assay tube (bio-related substance assay tube)
3: First microparticle
4: Second microparticle
5: Third microparticle
10: Tube chip body
12: Mount unit
13: Bio-related substance assay tube
14: Target substance capture bead (first microparticle)
15: Negative control bead (third microparticle)
16: Compensation bead (second microparticle)
17: Light-shielding bead
30: Quantification system
32: Central controller
34: Chip position controller
36: Light receiving unit
46: RAM
48: ROM
54: Signal processing circuit
56: Arithmetic unit for emission intensity
58: Arithmetic unit for compensated quantification
160: Bio-related substance assay tube
163: Target substance capture bead
165: First standard bead
167: Second standard bead
175: Quantification system
178: Calibration curve preparation unit
179: Arithmetic unit for quantification
200: Quantification system
202: Bio-related substance assay tube
204: Microparticle
206: Detection system
220: Dispensing nozzle
228: Central arithmetic unit
230: Laser light source
234: Fluorescence detector
235: Light separation system
240: Dichroic mirror
247: Arithmetic unit for quantification

The invention claimed is:

1. A quantification system for a bio-related substance, which comprises:
   a bio-related substance assay tube;
   a detection unit for detecting signals emitted from microparticles in the tube;
   wherein the microparticles comprises;
   a first microparticle on which a substance capable of binding to a target bio-related substance to be measured is immobilized, the first microparticle fixed in a first known position in the tube;
   a second microparticle on which the bio-related substance is immobilized in a given amount, the second microparticle fixed in a second known position in the tube; and
   a third microparticle for use as a negative control, the third microparticle fixed in a third known position in the tube,
   wherein these microparticles are aligned along the longitudinal direction of the tube, and
   wherein the detection unit moves relative to the tube along the longitudinal direction of the tube.

2. The quantification system according to claim 1, wherein the second microparticle is a microparticle used for compensation of data measured for the bio-related substance.

3. The quantification system according to claim 1, wherein the second microparticle comprises a plurality of microparticles on which different amounts of the bio-related substance are immobilized.

4. The quantification system according to claim 3, wherein the plurality of microparticles are microparticles used for preparation of a calibration curve.

5. The quantification system according to any one of claims 1 to 3, which further comprises light-shielding members interposed to separate the first to third microparticles.

6. The quantification system according to claim 1, which further comprises:
   a compensation unit for compensating data of the detected signals by referring to a calibration curve which has been prepared; and
   an arithmetic unit for quantifying the bio-related substance based on the compensated data.

7. The quantification system according to claim 1, which further comprises:
 a calibration curve preparation unit for preparing a calibration curve based on the detected signals; and
 an arithmetic unit for quantifying the bio-related substance by referring to the prepared calibration curve.

8. A method for measuring a bio-related substance by using the quantification system according to claim 1, which comprises contacting an analyte with the tube, and measuring the target bio-related substance in the analyte.

9. The quantification system according to claim 1, wherein the first, second and third microparticles are aligned one by one in line.

10. The quantification system according to claim 1, further comprising a light irradiation unit, the light irradiation unit and a light receiving unit are controlled for their movement.

* * * * *